United States Patent
Leuck et al.

(10) Patent No.: US 11,350,960 B2
(45) Date of Patent: Jun. 7, 2022

(54) DUAL STERILIZATION AND TEMPERATURE BASED STERILIZATION DETECTION

(71) Applicant: Ethicon LLC, Guaynabo, PR (US)

(72) Inventors: Stephen M. Leuck, Milford, OH (US); Ellen Burkart, Cincinnati, OH (US); Diana M. Castillo Sanchez, Stoughton, MA (US); Andrew W. Carroll, Cincinnati, OH (US); Sean P. Conlon, Loveland, OH (US); Rafael J. Ruiz Ortiz, Mason, OH (US); Demetrius N. Harris, Cincinnati, OH (US); Patrick J. Minnelli, Harrison, OH (US)

(73) Assignee: Cilag GmbH International, Zug (CH)

( * ) Notice: Subject to any disclaimer, the term of this patent is extended or adjusted under 35 U.S.C. 154(b) by 334 days.

(21) Appl. No.: 16/398,447

(22) Filed: Apr. 30, 2019

(65) Prior Publication Data

US 2020/0345880 A1    Nov. 5, 2020

(51) Int. Cl.
*A61B 17/32* (2006.01)
*A61L 2/28* (2006.01)
*A61B 17/00* (2006.01)

(52) U.S. Cl.
CPC ........ *A61B 17/320068* (2013.01); *A61L 2/28* (2013.01); *A61B 2017/0046* (2013.01); *A61B 2017/320074* (2017.08)

(58) Field of Classification Search
CPC .. A61B 17/320068; A61B 2017/32007; A61B 2017/320072; A61B 2017/320074; A61B 2017/320075; A61B 2017/320077; A61B 2017/32008; A61B 2017/320082;
(Continued)

(56) References Cited

U.S. PATENT DOCUMENTS

| 5,322,055 A | 6/1994 | Davison et al. |
| 5,324,299 A | 6/1994 | Davison et al. |
| 5,776,155 A | 7/1998 | Beaupre et al. |

(Continued)

FOREIGN PATENT DOCUMENTS

| EP | 1946708 B1 | 6/2011 |
| EP | 3 061 415 A1 | 8/2016 |

(Continued)

OTHER PUBLICATIONS

International Search Report and Written Opinion dated Jun. 19, 2020 for Application No. PCT/IB2020/053468, 11 pgs.

(Continued)

*Primary Examiner* — Wade Miles
(74) *Attorney, Agent, or Firm* — Frost Brown Todd LLC

(57) ABSTRACT

A surgical instrument includes a reusable assembly having an inner tube and an ultrasonic blade positioned within the inner tube. The inner tube includes at least one opening to receive a sterilization fluid therethrough for sterilizing the ultrasonic blade within the inner tube. The surgical instrument further includes a sterilization detection system to determine whether the reusable assembly has been sterilized during a sterilization cycle. A seal is selectively couplable with the at least one opening of the inner tube to fluidly seal the at least one opening for inhibiting bodily fluid from entering the at least one opening during a surgical procedure.

17 Claims, 20 Drawing Sheets

(58) Field of Classification Search
CPC ....... A61B 2017/320084; A61B 2017/320088; A61L 2/26; A61L 2/28
See application file for complete search history.

(56) References Cited

U.S. PATENT DOCUMENTS

| | | | |
|---|---|---|---|
| 5,873,873 A | 2/1999 | Smith et al. |
| 5,935,144 A | 8/1999 | Estabrook |
| 5,938,633 A | 8/1999 | Beaupre |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,189,233 B2 | 3/2007 | Truckai et al. |
| 7,186,253 B2 | 5/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,544,200 B2 | 6/2009 | Houser |
| 8,057,498 B2 | 11/2011 | Robertson |
| 8,461,744 B2 | 6/2013 | Wiener et al. |
| 8,591,459 B2 | 11/2013 | Clymer et al. |
| 8,591,536 B2 | 11/2013 | Robertson |
| 8,623,027 B2 | 1/2014 | Price et al. |
| 8,663,220 B2 | 3/2014 | Wiener et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 5/2016 | Houser et al. |
| 9,393,037 B2 | 7/2016 | Olson et al. |
| 9,795,379 B2 | 10/2017 | Leimbach et al. |
| 9,949,785 B2 | 4/2018 | Price et al. |
| 10,034,685 B2 | 7/2018 | Boudreaux et al. |
| 10,172,636 B2 | 1/2019 | Stulen et al. |
| 10,206,705 B2 | 2/2019 | Estera et al. |
| 10,327,797 B2 | 6/2019 | Conlon et al. |
| 10,492,820 B2 | 12/2019 | Hibner et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0105750 A1 | 4/2009 | Price et al. |
| 2011/0015660 A1 | 1/2011 | Wiener et al. |
| 2012/0116265 A1 | 5/2012 | Houser et al. |
| 2015/0080924 A1 | 3/2015 | Stulen et al. |
| 2015/0141981 A1 | 5/2015 | Price et al. |
| 2016/0143659 A1 | 5/2016 | Glutz et al. |
| 2017/0105751 A1* | 4/2017 | Hibner ........... A61B 17/320068 |
| 2019/0000499 A1 | 1/2019 | Stokes et al. |

FOREIGN PATENT DOCUMENTS

| | | |
|---|---|---|
| WO | WO 2015/073428 A1 | 5/2015 |
| WO | WO 2017/106230 A2 | 6/2017 |

OTHER PUBLICATIONS

U.S. Appl. No. 61/410,603, entitled "Energy-Based Surgical Instruments," filed Nov. 5, 2010.

* cited by examiner

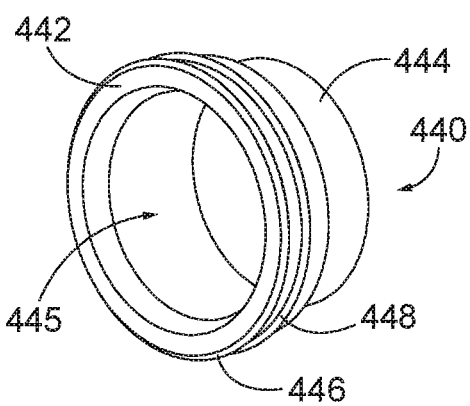
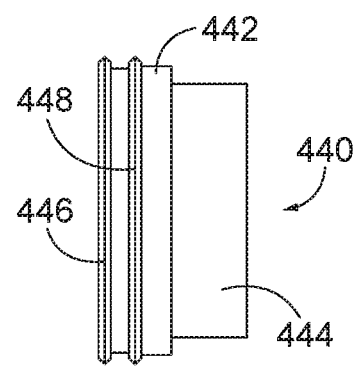
FIG. 8　　　　　FIG. 9
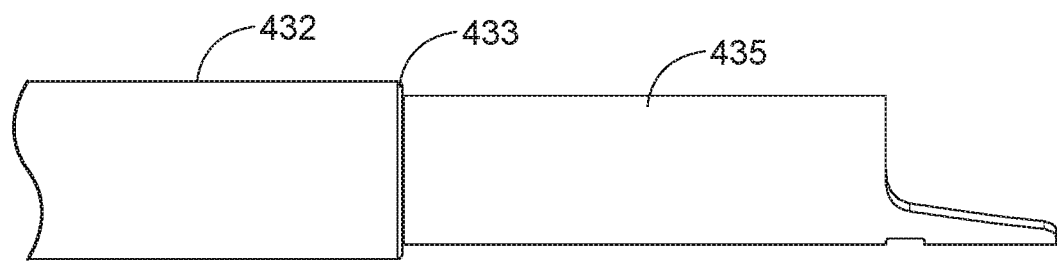
FIG. 10A
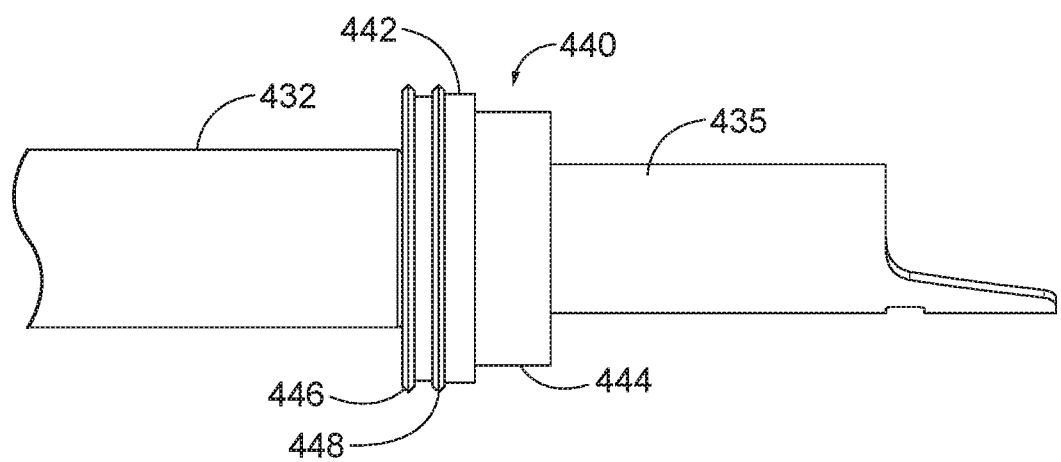
FIG. 10B

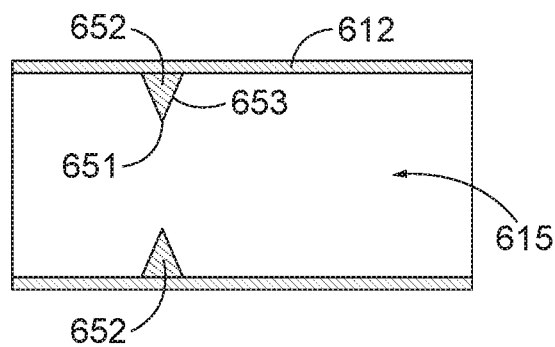
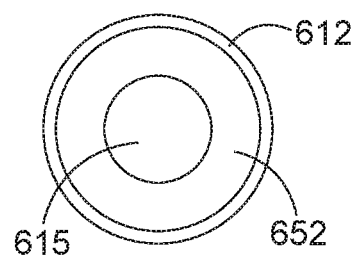
FIG. 19　　　　　　FIG. 20
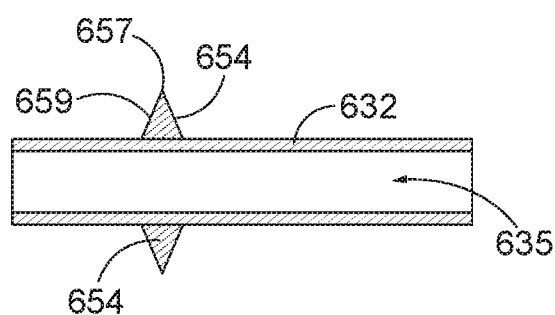
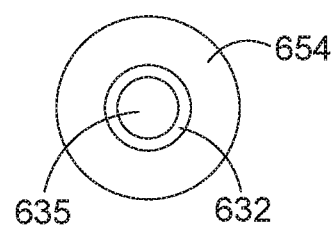
FIG. 21　　　　　　FIG. 22

DUAL STERILIZATION AND TEMPERATURE BASED STERILIZATION DETECTION

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; and U.S. Pat. No. 9,095,367, published Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of an outer seal for use with the reusable sub-assembly of FIG. 6A;

FIG. 9 depicts a side elevational view of the outer seal of FIG. 8;

FIG. 10A depicts a side elevational view of a distal end portion of an inner tube of the reusable sub-assembly of FIG. 6A;

FIG. 10B depicts a side elevational view of the distal end portion of the inner tube similar to FIG. 10A, but showing the outer seal of FIG. 8 assembled with the inner tube;

FIG. 19 depicts a cross-sectional view of a distal portion of the outer tube of FIG. 18 taken along a centerline thereof;

FIG. 20 depicts an end view of the outer tube of FIG. 18;

FIG. 21 depicts a cross-sectional view of a distal portion of an inner tube of the reusable sub-assembly of FIG. 18 taken along a centerline thereof;

FIG. 22 depicts an end view of the inner tube of FIG. 21;

Figure 1:
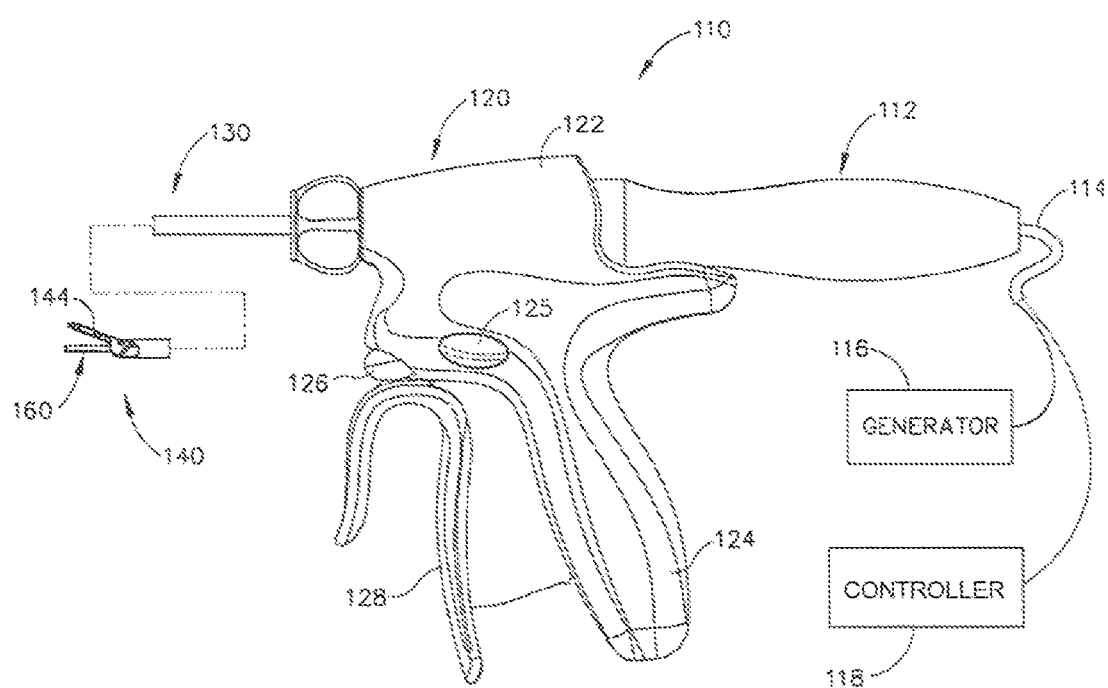
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. EXEMPLARY ULTRASONIC SURGICAL INSTRUMENT WITH INTEGRATED RF ENERGY

FIG. 1 illustrates an exemplary ultrasonic surgical instrument (110). At least part of instrument (110) may be constructed and operable in accordance with at least some of the teachings of any of the patent references that are cited herein. As described therein and as will be described in greater detail below, instrument (110) is operable to cut tissue and seal or weld tissue (e.g., a blood vessel, etc.) substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (125, 126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) are disclosed in various patent references cited herein; and further suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 1.

An ultrasonic transducer assembly (112) extends proximally from body (122) of handle assembly (120) in the present example. In some other versions, transducer assembly (112) is fully integrated within body (122). Transducer assembly (112) is coupled with a generator (116) via a cable (114). Transducer assembly (112) receives electrical power from generator (116) and converts that electrical power into ultrasonic vibrations through piezoelectric principles as is known in the art. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, controller (118) and generator (116) may be integrated together in a single unit. By way of example only, generator (116) may comprise a GEN04 or GEN11 sold by Ethicon Endo-Surgery, Inc. of Cincinnati, Ohio. In addition, or in the alternative, generator (116) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad that is secured to the underside of clamp arm (144), facing blade (160). By way of example only, the clamp pad may be formed of a polytetrafluoroethylene (PTFE) material and/or any other suitable material(s). By way of further example only, the clamp pad may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of trigger (128) toward pistol grip (124). Blade (160) of the present example is operable to vibrate at ultrasonic frequencies to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the acoustic waveguide and blade (160) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

End effector (140) of the present example is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (110) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition, or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pat. No. 9,949,785, entitled "Ultrasonic Surgical Instrument with Electrosurgical Feature," issued Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

Buttons (125, 126) may provide the operator with varied control of the energy that is applied to tissue through end effector (140). For instance, in some versions, button (125) may be activated to apply RF electrosurgical energy to tissue; while button (126) may be activated to apply ultrasonic energy to tissue. As another merely illustrative example, button (125) may be activated to apply ultrasonic energy to tissue at a low power level (e.g., without also applying RF electrosurgical energy to tissue, applying RF electrosurgical energy to tissue simultaneously, or applying RF electrosurgical energy to tissue in a sequence with the ultrasonic energy); while button (126) may be activated to apply ultrasonic energy to tissue at a high power level (e.g., without also applying RF electrosurgical energy to tissue, applying RF electrosurgical energy to tissue simultaneously, or applying RF electrosurgical energy to tissue in a sequence with the ultrasonic energy). In addition, or in the alternative, buttons (125, 126) may provide functionality in accordance with at least some of the teachings of U.S. Pat. No. 9,949,785, entitled "Ultrasonic Surgical Instrument with Electrosurgical Feature," issued Apr. 24, 2018, the disclosure of which is incorporated by reference herein. Other suitable ways in which buttons (125, 126) may provide operation of instrument (110) will be apparent to those of ordinary skill in the art in view of the teachings herein.

II. EXEMPLARY ULTRASONIC SURGICAL INSTRUMENT WITH COMBINATION OF REUSABLE AND DISPOSABLE COMPONENTS

In some instances, it may be desirable to provide a version of instrument (110) that is formed by a combination of components that are disposable (e.g., configured for use in only one surgical procedure) and components that are reusable (e.g., configured for use in more than one surgical procedure, subject to reprocessing and sterilization, etc., between surgical procedures). By way of example only, the disposable and reusable components of a surgical instrument may be assembled together to form the surgical instrument before a surgical procedure, the assembled surgical instrument may then be used to perform the surgical procedure, and then the disposable and reusable components of the surgical instrument may be disassembled after the surgical procedure is complete. Providing a disposable/reusable dichotomy among surgical instrument components may provide a reduction in cost and overall waste as compared to conventional instrumentations that are provided as an entirely disposable unit.

Figure 2:
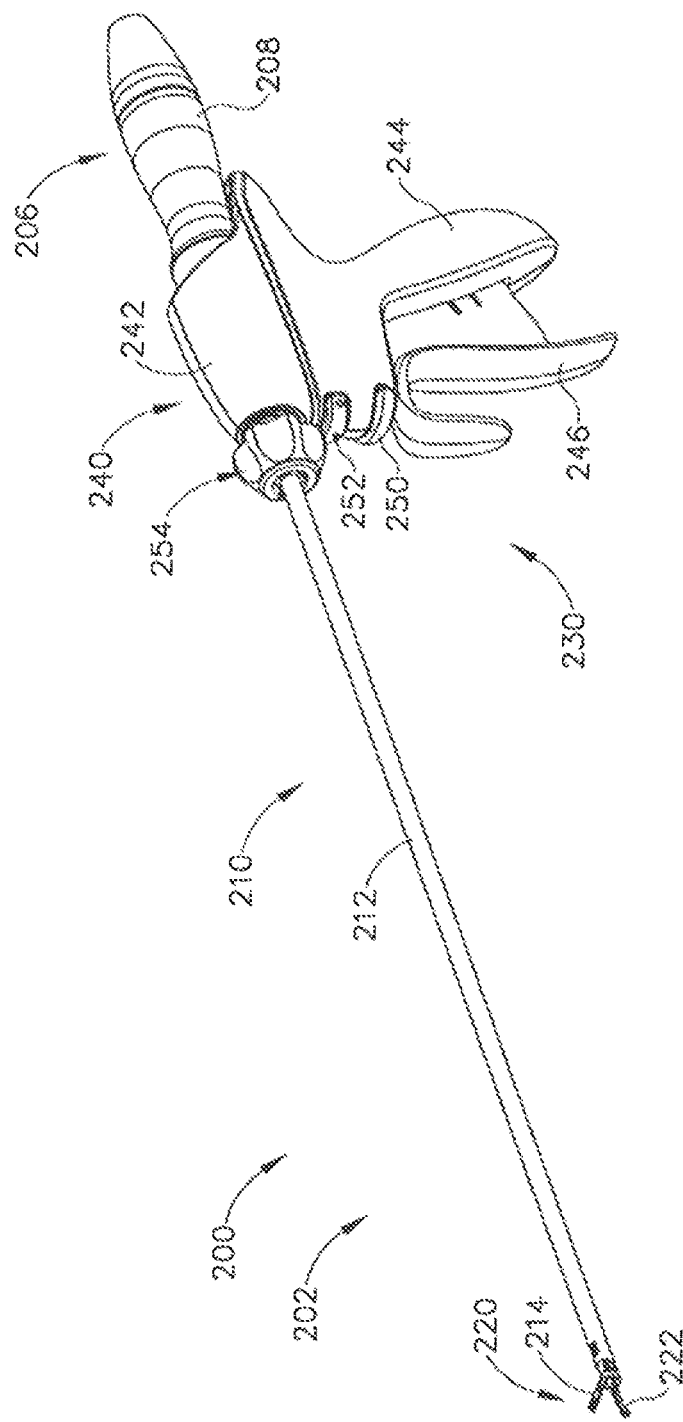
FIG. 2 depicts a perspective view of another exemplary ultrasonic surgical instrument, having a partially disposable assembly and a reusable assembly.
Figure 3:
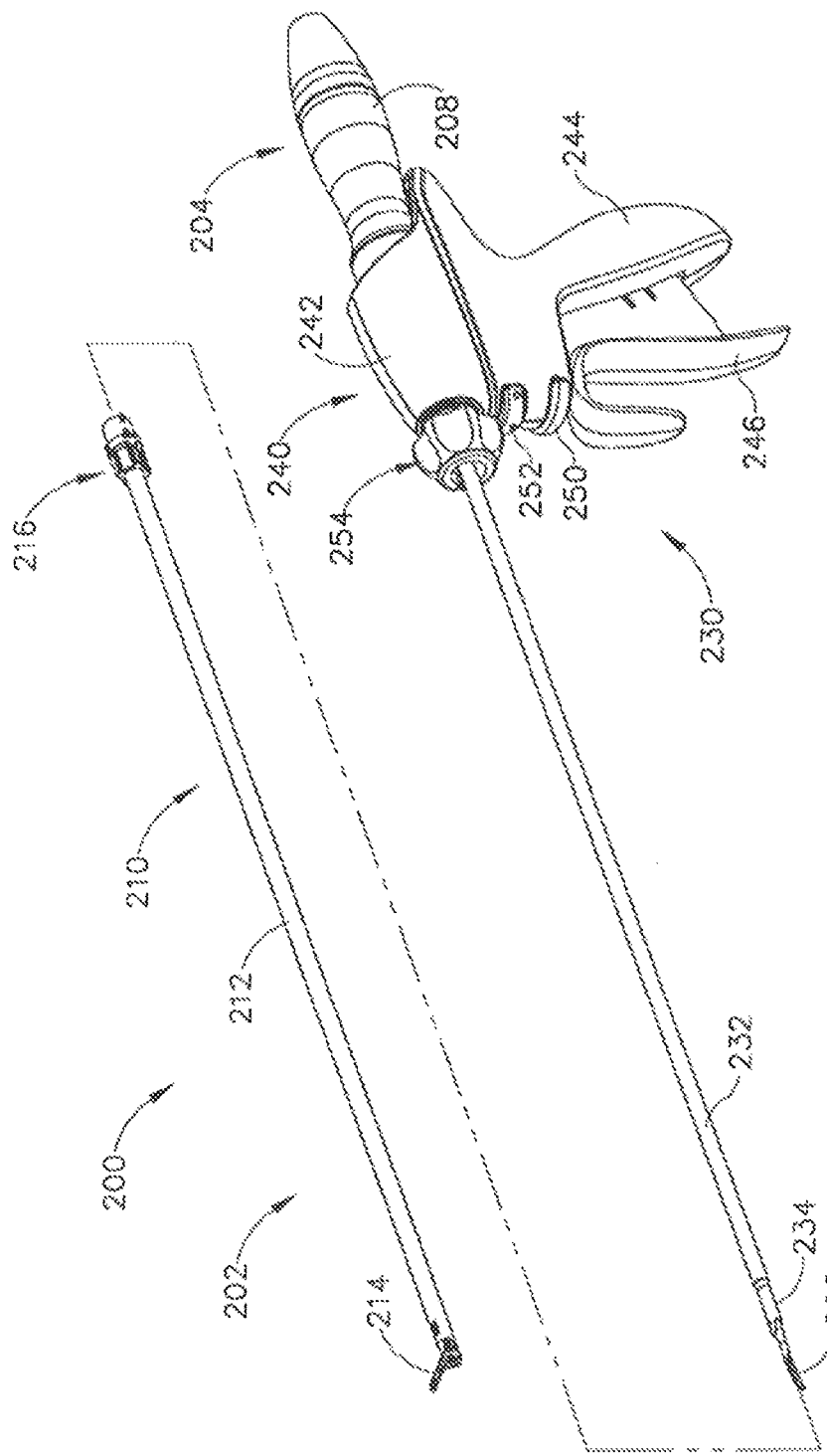
FIG. 3 depicts a partially exploded perspective view of the ultrasonic surgical instrument of FIG. 2, with an exemplary disposable sub-assembly separated from a first exemplary reusable sub-assembly of the partially disposable assembly.

FIGS. 2-3 show an exemplary variation of instrument (110) in the form of ultrasonic surgical instrument (200). Except as otherwise described below, ultrasonic surgical instrument (200) may be configured and operable just like instrument (110) described above and/or in accordance with any of the various teachings of the various patent references cited herein. Surgical instrument (200) is configured to be readily broken down into disposable and reusable components. In particular, surgical instrument (200) of this example comprises a reusable assembly (204) and a partially disposable assembly (202). When fully assembled, surgical instrument (200) provides an end effector (220) that includes an ultrasonic blade (222) and a clamp arm (214), which is pivotable toward and away from ultrasonic blade (222). End effector (220) is thus operable to grasp, ultrasonically seal, and ultrasonically sever tissue as described herein and as described in various references cited herein.

Reusable assembly (204) comprises an ultrasonic transducer (208), which is operable to convert electrical power into ultrasonic vibrations, also as described herein and as described in various references cited herein. Ultrasonic transducer (208) is acoustically coupled with ultrasonic blade (222) via an acoustic waveguide (234), a portion of which is shown in FIG. 3. It should be understood that ultrasonic transducer (208), ultrasonic blade (222), and acoustic waveguide (234) may be configured in accordance with the teachings of any of the various references cited herein; or in any other suitable fashion.

Partially disposable assembly (202) of the present example comprises an exemplary disposable sub-assembly (210) and a first exemplary reusable sub-assembly (230). Sub-assemblies (210, 230) are configured to be coupled together to form partially disposable assembly (202), which may then be coupled with reusable assembly (204) for form a complete ultrasonic surgical instrument (200). As shown in FIG. 3, disposable sub-assembly (210) comprises an outer tube (212). Clamp arm (214) is pivotally coupled with a distally projecting tongue of outer tube (212). A coupling member (216) is fixedly secured to the proximal end of outer tube (212). Disposable sub-assembly (210) further comprises a distal inner tube member (not shown), which is slidably and coaxially disposed within the distal end of outer tube (212). This distal inner tube member (not shown) is also pivotally coupled with clamp arm (214) via a distally projecting tongue of the distal inner tube member (not shown). Thus, when outer tube (212) translates longitudinally relative to the distal inner tube member (not shown), clamp arm (214) will pivot toward and away from ultrasonic blade (222). As used herein, the term "sub-assembly" refers to a plurality of components arranged together that may be, in the present example, a portion of a larger assembly of components. In this respect, the term "sub-assembly" may also be referred to as an "assembly. It will thus be appreciated that the term "sub-assembly" is not intended to unnecessarily limit the invention described herein.

Reusable sub-assembly (230) of the present example comprises a handle assembly (240), a proximal inner tube member (232), acoustic waveguide (234), and ultrasonic blade (222). Proximal inner tube member (232) is configured to removably couple with the distal inner tube member (not shown) of disposable sub-assembly (210) first when sub-assemblies (210, 230) are assembled together. When proximal inner tube member (232) is coupled with the distal inner tube member (not shown) of disposable sub-assembly (210), inner tube members (not shown, 232) remain longitudinally stationary relative to handle assembly (240).

Handle assembly (240) comprises a housing (242) that defines a pistol grip (244). Handle assembly (240) further includes a trigger (246) that is pivotable toward and away from pistol grip (244); and a pair of buttons (250, 252). Buttons (250, 252) are operable to activate ultrasonic transducer (208) to thereby activate ultrasonic blade (222). In particular, one button (250) will provide activation of ultrasonic blade (222) at one power level or profile; while the other button (252) will provide activation of ultrasonic blade (222) at another power level or profile. Of course, any other suitable user input feature(s) may be used. It should also be understood that handle assembly (240) may be modified to include a feature that is operable to activate RF electrosurgical energy at end effector (220) (e.g., like button (125) described above).

Trigger (246) is operable to actuate clamp arm (214), such that clamp arm (214) will pivot toward ultrasonic blade (222) when trigger (246) us pivoted toward pistol grip (244); and such that clamp arm (214) will pivot away from ultrasonic blade (222) when trigger (246) us pivoted away from pistol grip (244). In the present example, this movement is provided by translating outer tube (212) longitudinally relative to housing (242) in response to pivotal movement of trigger (246), while inner tube members (not shown, 232) remain longitudinally stationary relative to housing (242). Various suitable ways in which outer tube (212) may be translated longitudinally in response to pivotal movement of trigger (246) will be apparent to those of ordinary skill in the art in view of the teachings herein. It should also be understood that, in some alternative versions, clamp arm (214) is pivoted by translating inner tube members (not shown, 232) longitudinally relative to housing (242) while outer tube (212) remains longitudinally stationary relative to housing (242).

As shown in FIGS. 2-3, handle assembly (240) of the present example further includes a knob member (254). Knob member (254) is rotatable relative to housing (242). When instrument (200) is fully assembled, knob member (254) is coupled with acoustic waveguide (234), inner tube members (not shown, 232), and outer tube (212) such that these components will rotate together unitarily relative to housing (242). Knob member (254) also provides guidance to disposable sub-assembly (210) when disposable sub-assembly (210) is being coupled with reusable sub-assembly (230). By way of example only, knob member (254) may be configured and operable in accordance with the teachings of any of the various references cited herein.

After ultrasonic surgical instrument (200) is used in a surgical procedure, reusable assembly (204) may be removed from partially disposable assembly (202). After reusable assembly (204) is removed from partially disposable assembly (202), disposable sub-assembly (210) is then be removed from reusable sub-assembly (230). Reusable assembly (204), disposable sub-assembly (210), and reusable sub-assembly (230) may then be subject to different kinds of processing. Examples of such subsequent processing are described below, while other examples will be apparent to those of ordinary skill in the art in view of the teachings herein.

In some instances, reusable assembly (204) may be cleaned, sterilized, and re-used up to 100 times (by way of example only). Disposable sub-assembly (210) may be disposed of immediately, such that disposable sub-assembly (210) is only used in one single surgical procedure. By way of example, reusable sub-assembly (230) may be cleaned, sterilized, and re-used in different surgical procedures between 2 to 20 times, although it will be appreciated that any such number of times, also referred to herein as cycles, may be similarly used as desired. Of course, these re-use scenarios are merely illustrative examples. It should nevertheless be understood that the configuration of partially disposable assembly (202) may minimize the amount of single-use material that is disposed of after each surgical procedure. It should also be understood that, in some variations, partially disposable assembly (202) is simply disposed of as a single unit. In other words, in some variations, partially disposable assembly (202) is not configured to be disassembled into disposable sub-assembly (210) and reusable sub-assembly (230).

By way of example only, as part of the post-surgery processing for re-use, reusable assembly (204) and/or reusable sub-assembly (230) may be sterilized in a conventional relatively low temperature, relatively low pressure, hydrogen peroxide sterilization process (e.g., in a STERRAD® sterilizing system by Advanced Sterilization Products of Irvine, Calif.). Alternatively, reusable assembly (204) and/or reusable sub-assembly (230) may be sterilized using any other suitable systems and techniques.

In addition to the foregoing, instrument (200) may be constructed and operable in accordance with at least some of the teachings of U.S. patent application Ser. No. 15/270,540, entitled "Ultrasonic Surgical Instrument with Removable Shaft Assembly Portion," filed Sep. 20, 2016, issued as U.S. Pat. No. 10,327,797 on Jun. 25, 2019, the disclosure of which is incorporated by reference herein; and/or U.S. patent application Ser. No. 15/270,600, entitled "Ultrasonic Surgical Instrument with Removable Shaft Assembly Portion," filed Sep. 20, 2016, issued as U.S. Pat. No. 10,492,820 on Dec. 3, 2019, the disclosure of which is incorporated by reference herein. In addition, or in the alternative, instrument (200) may be constructed and operable in accordance with at least some of the teachings of any of the various patent references cited herein.

III. EXEMPLARY ULTRASONIC SURGICAL INSTRUMENTS WITH DUAL STERILIZATION AND TEMPERATURE BASED STERILIZATION DETECTION

As discussed above, as part of the post-surgery processing for re-use, reusable assembly (204) and/or reusable sub-assembly (230) may be sterilized in a conventional relatively low temperature, relatively low pressure, hydrogen peroxide gas sterilization process (e.g., in a STERRAD® sterilizing system by Advanced Sterilization Products of Irvine, Calif.). Alternatively, reusable assembly (204) and/or reusable sub-assembly (230) may be sterilized via an autoclave system by using pressurized saturated steam at an elevated temperature. Still any other suitable systems and techniques may be used to sterilize reusable assembly (204) and/or reusable sub-assembly (230). After sterilization, reusable assembly (204) and/or reusable sub-assembly (230) may be assembled with another disposable sub-assembly (210) for re-use in another surgical procedure.

In some instances, it may be desirable to track the number of sterilization cycles reusable assembly (204) and/or reusable sub-assembly (230) has endured, because such information may be used to make reliability predictions for reusable assembly (204) and/or reusable sub-assembly (230). In some instances, it may also be desirable to sterilize reusable sub-assembly (230) in an assembled state without having to remove ultrasonic blade (222) from inner tube (232), which may provide for a more efficient and/or simpler sterilization process. Accordingly, an exemplary system (310) as well as various examples of reusable assemblies (430, 530, 630, 730, 830) with dual sterilization and/or temperature based sterilization detection will be discussed in more detail below and may be incorporated in whole, or in part, into surgical instruments (110, 200) discussed above.

A. Exemplary Temperature Based Sterilization Detection

Figure 4:
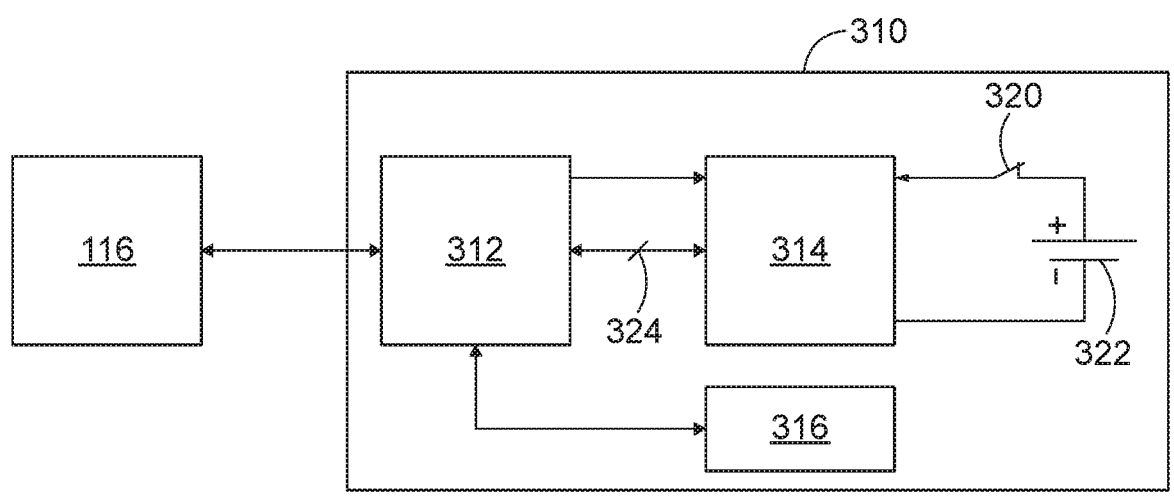
FIG. 4 depicts a diagrammatic view of a sterilization detection system that may be incorporated into the reusable assembly and/or the reusable sub-assembly of the partially disposable assembly of FIG. 3.

Referring to FIG. 4, an exemplary temperature based sterilization detection system (310) is shown that may be incorporated into reusable assembly (204) (see FIG. 3) and/or reusable sub-assembly (230) (see FIG. 3) of surgical instrument (200) (see FIG. 3). Sterilization detection system (310) may track total elapsed time reusable assembly (204) (see FIG. 3) and/or reusable sub-assembly (230) (see FIG. 3) has been subjected to temperatures exceeding a predetermined threshold such as during a sterilization cycle. Sterilization detection system (310) may then relay this information when surgical instrument (200) (see FIG. 3) is coupled with generator (116) as discussed above. As shown in FIG. 4, sterilization detection system (310) comprises controller (312) connected with memory (316) and clock (314) via interface (324). Clock (314) is then connected with thermal switch (320) and battery (322).

Controller (312) is configured to determine the number of sterilization cycles reusable assembly (204) (see FIG. 3) and/or reusable sub-assembly (230) (see FIG. 3) have undergone. Controller (312) may include a microcontroller, an application-specific integrated circuit (ASIC), or other suitable device for making such determinations. Memory (316) may include an EEPROM or other suitable device to store information needed by controller (312) to determine the number of sterilization cycles, such as the predetermined temperature threshold and/or various amounts of time needed for performing various types of sterilization cycles in various conditions. In another example, memory (316) may be writable such that memory (316) is also configured to store information determined by controller (312) for future use. Clock (314) may include a real time clock configured to count the amount of time reusable assembly (204) (see FIG. 3) and/or reusable sub-assembly (230) (see FIG. 3) stays above the predetermined temperature threshold. An example of a real time clock that may be used with sterilization detection system (310) is a PCA8565TS/1 clock provided by NXP Semiconductors of the Netherlands and/or a MCP7940N clock provided by Microchip Technology Inc. of Chandler, Ariz. Interface (324) is configured to send communications between clock (314) and controller (312). Some examples of an interface (324) is a serial peripheral interface (SPI) or an inter-integrated circuit ($I^2C$). Thermal switch (320) may be normally open and have a trip point at the predetermined temperature threshold to close thermal switch (320). Such a predetermined temperature threshold may be between about 100° C. and about 130° C. In some versions, the predetermined temperature threshold is adjustable based on operating conditions. Battery (322) is configured to supply power to sterilization detection system (310) such as when sterilization detection system (310) is not coupled with generator (300). Battery (322) may include a coin cell battery. An example of battery (322) is a BR2450 battery provided by Panasonic Corporation of Osaka, Japan. Still other suitable components for use with sterilization detection system (310) will be apparent to one with ordinary skill in the art in view of the teachings herein.

Figure 5:
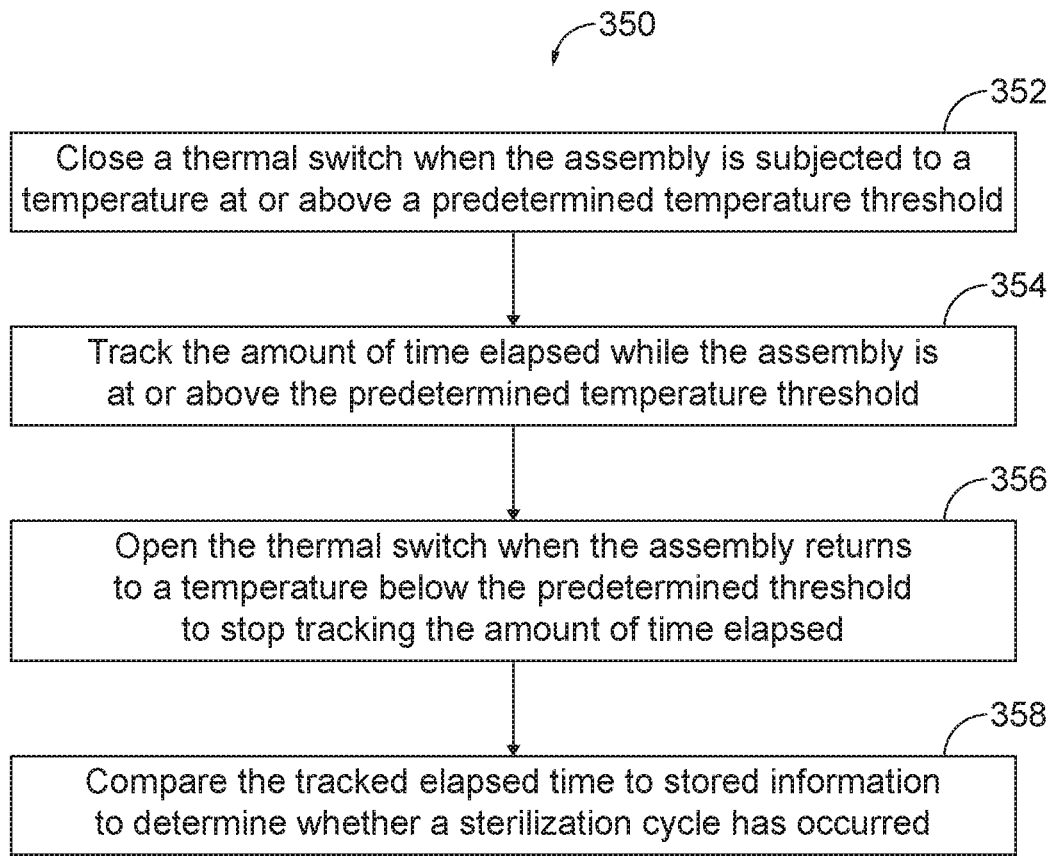
FIG. 5 depicts a flowchart of a method for operating the sterilization detection system of FIG. 4.

During use, sterilization detection system (310) is configured to track total elapsed time reusable assembly (204) (see FIG. 3) and/or reusable sub-assembly (230) (see FIG. 3) has been subjected to temperatures exceeding the predetermined threshold to determine the number and/or type of sterilization cycle reusable assembly (204) (see FIG. 3) and/or reusable sub-assembly (230) (see FIG. 3) has undergone. A method (350) of operating sterilization detection system (310) is shown in FIG. 5 with further reference to FIG. 4. In step (352), thermal switch (320) is in a normally open position and switches to a closed position when thermal switch (320) is subjected to a temperature above the predetermined temperature threshold to close a connection between battery (322) and clock (314). Battery (322) then powers clock (314) as long as the temperature stays above the predetermined temperature threshold to direct clock (314) to count the number of elapsed minutes or hours, as shown in step (354). When the temperature falls back below the predetermined temperature threshold, such as when the sterilization cycle has ended, thermal switch (320) returns to the open position to disconnect battery (322) from clock (314) and thereby stop clock (314), as shown in step (356). Clock (314) then communicates the amount of elapsed time to controller (312) through interface (324). Controller (312) then compares this elapsed time to information stored by memory (316) to determine: 1) whether a sterilization cycle has been performed if the time has incremented, 2) the number of sterilization cycles performed, and/or 3) the type of sterilization cycle that has been performed, as shown in step (358). For instance, sterilization detection system (310) determines the difference between a deep sterilization cycle and a flash sterilization cycle based on the amount of elapsed time. In some examples, this information is then stored by memory (316) for future use. Sterilization detection system (310) then relays this information to a user when surgical instrument (200) (see FIG. 3) is coupled with generator (116) such as to perform a surgical procedure. Still other suitable methods for detecting a sterilization cycle will be apparent to one with ordinary skill in the art in view of the teachings herein.

In some variations, sterilization detection system (310) may decrease and/or eliminate false sterilization increments. Previously, generator (116) incremented a sterilization counter (not shown) when surgical instrument (200) (see FIG. 3) was disconnected and then re-connected to generator (116). In some instances, components of surgical instrument (200) (see FIG. 3) may not have been sterilized while surgical instrument (200) (see FIG. 3) was disconnected from generator (116). The sterilization counter (not shown) may thereby have been incremented without a sterilization cycle having been performed. Alternatively, sterilization detection system (310) may confirm whether a sterilization cycle has been performed based on the amount of elapsed time reusable assembly (204) (see FIG. 3) and/or reusable sub-assembly (230) (see FIG. 3) has been above a predetermined temperature threshold to increment a sterilization counter (not shown). By decreasing and/or eliminating false sterilization increments, the number of uses of reusable assembly (204) (see FIG. 3) and/or reusable sub-assembly (230) (see FIG. 3) may be extended.

B. Exemplary Perforated Inner Tube

Referring to FIGS. 6A-13B, a second exemplary reusable sub-assembly (430) is shown that is similar to reusable sub-assembly (230) (see FIG. 3) described above, except that inner tube (432) of reusable sub-assembly (430) comprises perforations (436) to allow reusable sub-assembly (430) to be sterilized with ultrasonic blade (422) assembled with inner tube (432). For instance, as best shown in FIG. 6B, inner tube (432) comprises at least one opening, such as one or more perforations (436), extending through a sidewall of inner tube (432). In the illustrated example, perforations (436) have a generally oval shape, but other suitable shapes may used, such as rectangular, square, circular, etc. In one version, perforations (436) are aligned longitudinally along inner tube (432) to form a row of perforations (436). These rows of perforations (436) may positioned angularly about a circumference of inner tube (432) to form two or more rows of perforations (436). In some other versions, perforations (436) may be formed in other suitable positions about inner tube (432), such as in staggered and/or random positions. Accordingly, perforations (436) allow sterilization fluid or gas to diffuse from outside of inner tube (432), through perforations (436) of inner tube (432), and to ultrasonic blade (422).

Figure 7A:
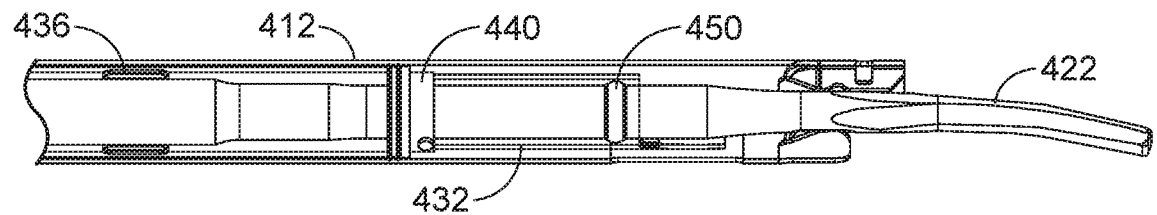
FIG. 7A depicts a cross-sectional view of the distal end portion of the reusable sub-assembly coupled with the outer tube of FIG. 6A taken along section line 7A-6=7A of FIG. 6A.
Figure 7B:
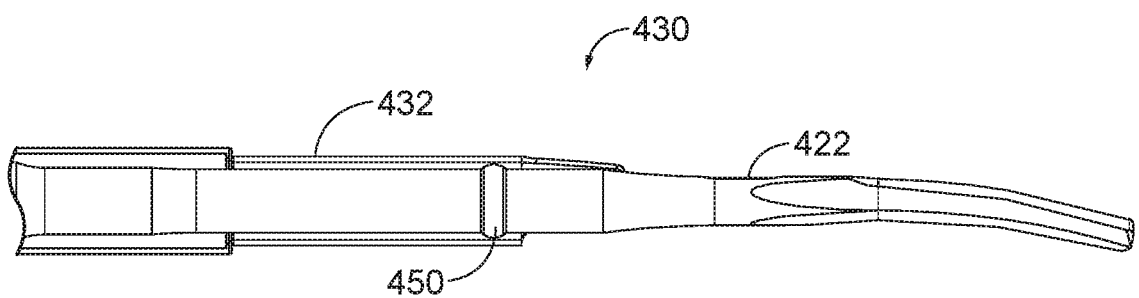
FIG. 7B depicts a cross-sectional view of the distal end portion of the reusable sub-assembly similar to FIG. 6A, taken along section line 7B-7B of FIG. 6B, but having the outer tube removed therefrom.

While it may be desirable to provide perforations (436) during sterilization, perforations (436) may be sealed during a surgical procedure to inhibit bodily fluid from entering into a distal portion of inner tube (432) and/or outer tube (412). Accordingly, as shown in FIGS. 7A and 7B, outer seal (440) and inner seal (450) are provided between inner tube (432) and outer tube (412) and between ultrasonic blade (422) and inner tube (432), respectively.

Referring to FIGS. 8-9, outer seal (440) comprises a generally circular shape defined by proximal annular flange (442) and distal annular flange (444) positioned distal to proximal annular flange (442). Proximal annular flange (442) and distal annular flange (444) define opening (445) extending through proximal annular flange (442) and distal annular flange (444) and configured to receive inner tube (432). In the illustrated example, proximal annular flange (442) has a larger outer diameter than distal annular flange (444). Proximal annular flange (442) further comprises proximal sealing member (446) and distal sealing member (448) positioned about proximal annular flange (442) configured to abut an inner surface of outer tube (412) (see FIG. 7A) when outer tube (412) (see FIG. 7A) is assembled with inner tube (432) (see FIG. 7A). Proximal sealing member (446) and/or distal sealing member (448) may be an o-ring style seal comprising an elastomeric material such as silicone or other suitable material. Accordingly, outer seal (440) may be positioned about distal portion (435) of inner tube (432) such that outer seal (440) is adjacent to annular flange (433) of inner tube (342) distal of perforations (436), as shown in FIGS. 10A-10B. Outer seal (440) may thereby inhibit bodily fluid from entering distally between inner tube (432) and outer tube (412).

Figure 11:
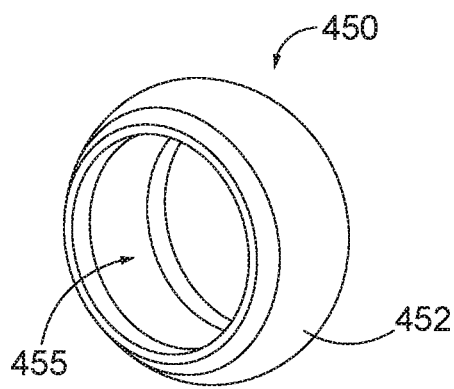
FIG. 11 depicts a perspective view of an inner seal of the reusable sub-assembly of FIG. 6A.
Figure 12:
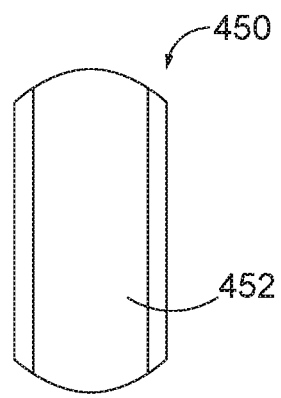
FIG. 12 depicts a side elevational view of the inner seal of FIG. 11.
Figure 13A:
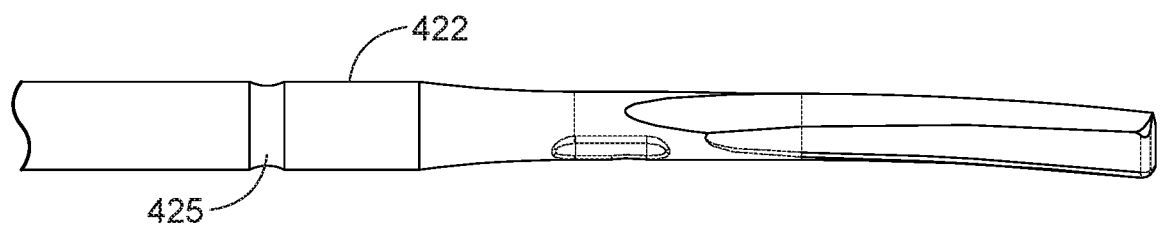
FIG. 13A depicts a side elevational view of a distal end portion of an ultrasonic blade of the reusable sub-assembly of FIG. 6A.
Figure 13B:
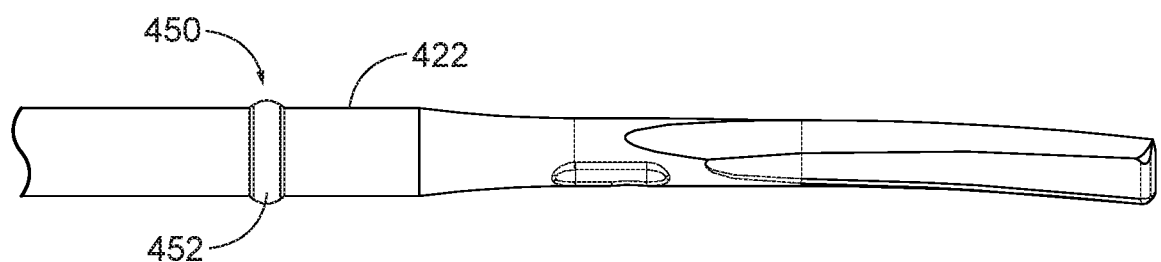
FIG. 13B depicts the side elevational view of the distal end portion of the ultrasonic blade of the reusable sub-assembly similar to FIG. 13A, but showing the inner seal of FIG. 11 assembled with the ultrasonic blade.
Figure 14:
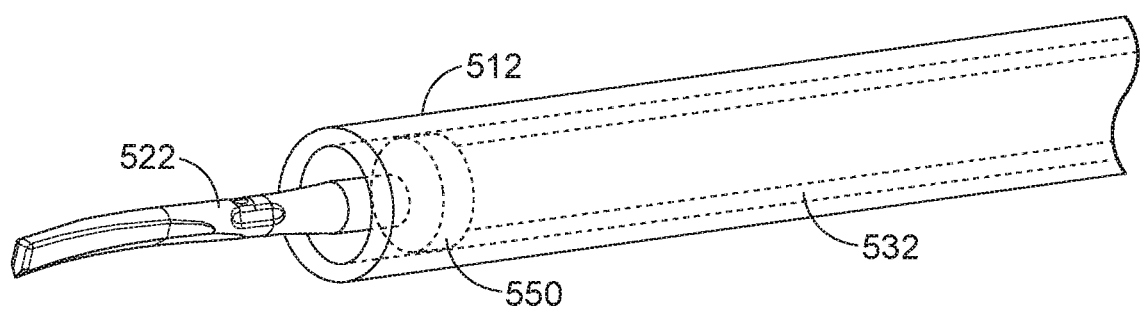
FIG. 14 depicts a perspective view of a distal end portion of a third exemplary reusable sub-assembly coupled with an outer tube comprising a distal seal.

Inner seal (450) comprises a generally circular shape defined by sidewall (452), as shown in FIGS. 11-12. Sidewall (452) may comprise an arcuate shape such that a central portion of sidewall (452) extends outward relative to end portions of sidewall (452). Sidewall (452) defines opening (455) extending through sidewall (452) configured to receive ultrasonic blade (422). Inner seal (450) may be an o-ring style seal comprising an elastomeric material such as silicone or other suitable material. Accordingly, inner seal (450) may be positioned about distal portion of ultrasonic blade (422) about indent (425) of ultrasonic blade (422) extending inwardly on ultrasonic blade (422) such that inner seal (450) is distal of perforations (436), as shown in FIGS. 13A-13B. Inner seal (450) may thereby inhibit bodily fluid from entering distally between ultrasonic blade (422) and inner tube (432). Still other suitable configurations for sealing reusable sub-assembly (430) (see FIG. 6B) will be apparent to one with ordinary skill in the art in view of the teachings herein.

In use, during a surgical procedure, reusable sub-assembly (430) is assembled with outer tube (412). Referring back to FIGS. 6A and 7A, outer tube (412) is positioned about inner tube (432) to cover perforations (436) such that outer tube (412) acts as a sheath. Outer seal (440) is then positioned about distal portion (435) of inner tube (432) such that outer seal (440) is adjacent to annular flange (433) of inner tube (342) distal of perforations (436). Outer seal (440) thereby inhibits bodily fluid from entering distally between inner tube (432) and outer tube (412). Inner seal (450) is positioned about distal portion of ultrasonic blade (422) about indent (425) of ultrasonic blade (422) such that inner seal (450) is distal of perforations (436). Inner seal (450) thereby inhibits bodily fluid from entering distally between ultrasonic blade (422) and inner tube (432).

Figure 6A:
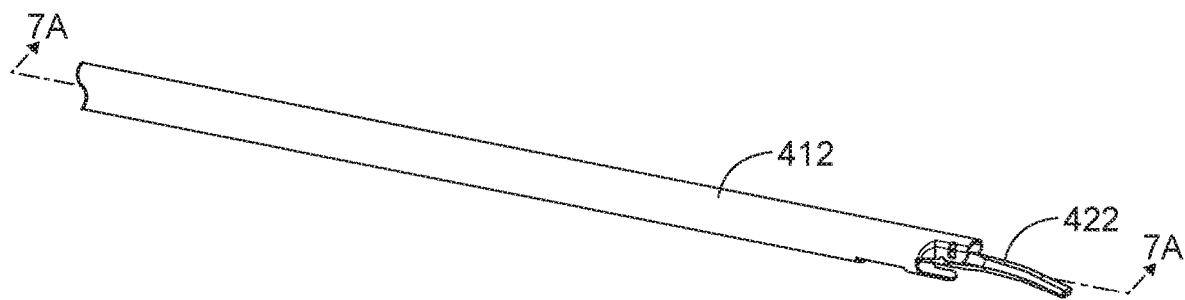
FIG. 6A depicts a perspective view of a distal end portion of a second exemplary reusable sub-assembly coupled with an outer tube.
Figure 6B:
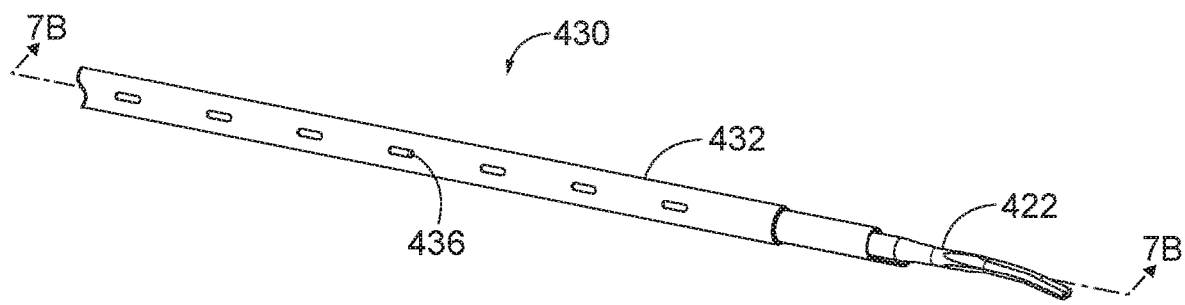
FIG. 6B depicts the perspective view of the distal end portion of the reusable sub-assembly similar to FIG. 6A, but having the outer tube removed therefrom.

After the surgical procedure, outer tube (412) and outer seal (440) are removed from reusable sub-assembly (430), as shown in FIGS. 6B and 7B. Inner seal (450) remains positioned between inner tube (432) and ultrasonic blade (422). Reusable sub-assembly (430) is then sterilized such that inner tube (432) is assembled with ultrasonic blade (422). During sterilization, sterilization fluid, such as a sterilization gas, diffuses through perforations (436) of inner tube (432) to effectively sterilize ultrasonic blade (422). Once sterilization is complete, reusable sub-assembly (430) is coupled with another outer tube (412) and outer seal (440) for reuse. In some versions, outer seal (440) is coupled with an inner surface of outer tube (412) to place outer seal (440) about inner tube (432) when outer tube (412) is assembled with inner tube (432). Still other suitable configurations for sterilizing reusable sub-assembly (430) will be apparent to one of ordinary skill in the art in view of the teachings herein.

C. Exemplary Outer Tube Distal Seal

Figure 15:
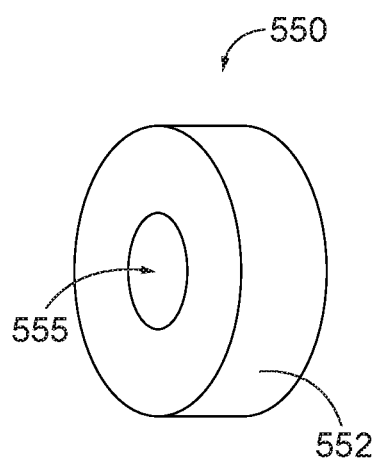
FIG. 15 depicts a perspective view of the distal seal of FIG. 14.
Figure 16:
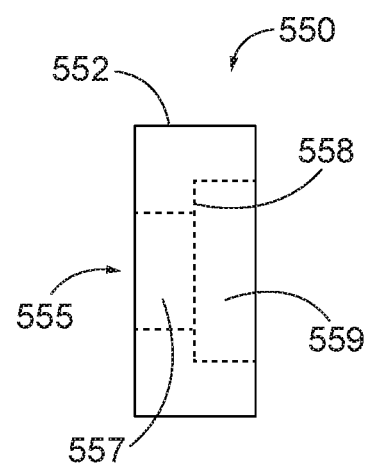
FIG. 16 depicts a side elevational view of the distal seal of FIG. 14.

Referring to FIGS. 14-17B, a third exemplary reusable sub-assembly (530) as well as an exemplary alternative outer tube (512) is shown that is similar to outer tube (212) (see FIG. 3) described above, except that outer tube (512) comprises distal seal (550) that is removable from inner tube (532) when outer tube (512) is removed from inner tube (532). As best shown in FIGS. 15-16, distal seal (550) includes a generally circular body (552) defining opening (555) therethrough. Opening (555) comprises distal opening (557) and proximal opening (559) having a larger outer diameter than distal opening (557) to form ridge (558) on the interior surface of body (552) between distal opening (557) and proximal opening (559). Distal seal (550) may comprise an elastomeric material such as silicone or other suitable material. Distal seal (550) may be coupled with an interior surface of a distal portion of outer tube (512).

Figure 17A:
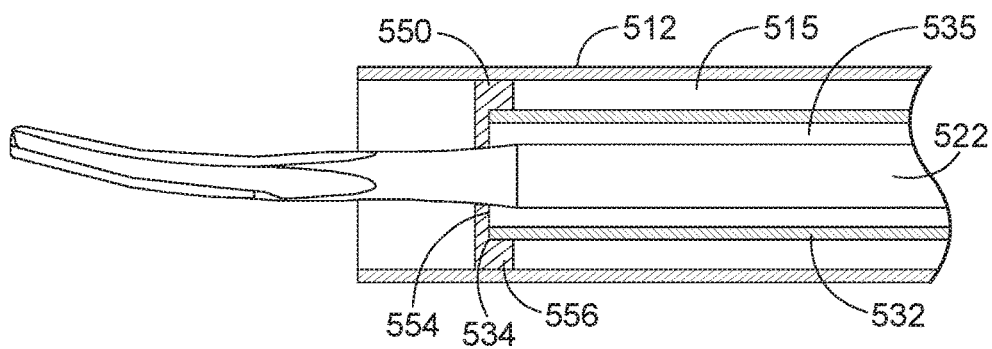
FIG. 17A depicts a sectional view of the distal end portion of the reusable sub-assembly of FIG. 14, taken generally along a centerline thereof, assembled with the outer tube.

In use, outer tube (512) is positioned about inner tube (532) and ultrasonic blade (522) for a surgical procedure, as shown in FIG. 17A. In this assembled configuration, distal end (534) of inner tube (532) is inserted within proximal opening (559) of distal seal (550) to abut ridge (558). Ultrasonic blade (522) then extends through inner tube (532) and distal opening (557) of distal seal (550). Distal seal (550) thereby extends from ultrasonic blade (522) to outer tube (512) to cover distal end (534) of inner tube (532) and seal opening (535) between ultrasonic blade (522) and inner tube (532), and opening (515) between inner tube (532) and outer tube (512). This inhibits bodily fluid from entering distally between ultrasonic blade (522), inner tube (532), and/or outer tube (512).

Figure 17B:
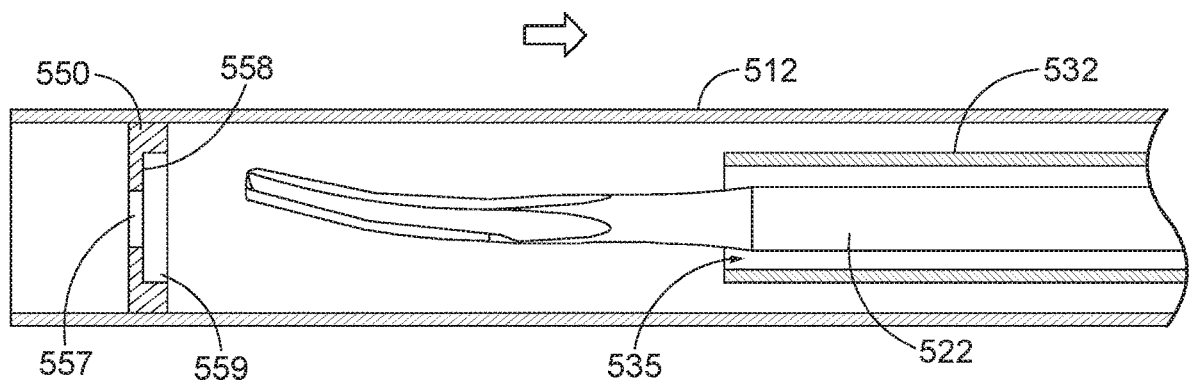
FIG. 17B depicts the sectional view of the distal end portion of the reusable sub-assembly similar to FIG. 14, but showing the reusable sub-assembly being removed from the outer tube.
Figure 18:
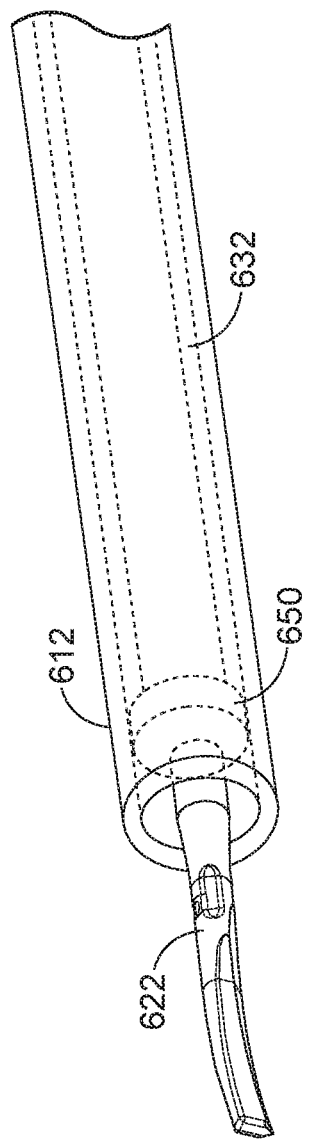
FIG. 18 depicts a perspective view of a distal end portion of a fourth exemplary reusable sub-assembly coupled with an outer tube.

After the surgical procedure, outer tube (512) is removed from inner tube (532) and ultrasonic blade (522), as shown in FIG. 17B, to thereby remove distal seal (550) with outer tube (512). With distal seal (550) removed, inner tube (532) and ultrasonic blade (522) are sterilized. During sterilization, sterilization fluid, such as sterilization gas, diffuses between inner tube (532) and ultrasonic blade (522) through distal opening (535) of inner tube (532) to thereby effectively sterilize ultrasonic blade (522). Once sterilization is complete, inner tube (532) and ultrasonic blade (522) are coupled with another outer tube (512) and distal seal (550) for reuse. Still other suitable configurations for distal seal (550) will be apparent to one of ordinary skill in the art in view of the teachings herein.

D. Exemplary Split Seal Between Inner and Outer Tube

Referring to FIGS. 18-23B, a fourth exemplary reusable sub-assembly (630) as well as another exemplary alternative outer tube (612) and inner tube (632) is shown that are similar to outer tube (212) (see FIG. 3) and inner tube (232) (see FIG. 3) described above, except that outer tube (612) and inner tube (632) comprise split seal (650) between outer tube (612) and inner tube (632). Split seal (650) comprises inner seal (652), extending inwardly within opening (615) of outer tube (612), and outer seal (654), extending outwardly from inner tube (632). As shown in FIGS. 19-20, inner seal (652) defines a generally triangular shape extending within a circumference of outer tube (612) to form tip (651) of inner seal (652) within opening (615) of outer tube (612). Inner seal (652) further defines proximal wall (653) extending transversely within opening (615) of outer tube (612). As shown in FIGS. 21-22, outer seal (654) is shaped to correspond with inner seal (652) to define a generally triangular shape extending about a circumference of inner tube (632) to form tip (657) of outer seal (654). Outer seal (654) further defines distal wall (659) extending transversely from inner tube (632) at a similar angle as proximal wall (653) of inner seal (652). Inner and/or outer seal (652, 654) may comprise an elastomeric material such as silicone or other suitable material. Accordingly, inner seal (652) and outer seal (654) may be selectively coupled to form a seal between outer tube (612) and inner tube (632) when outer tube (612) is assembled with inner tube (632).

Figure 23A:
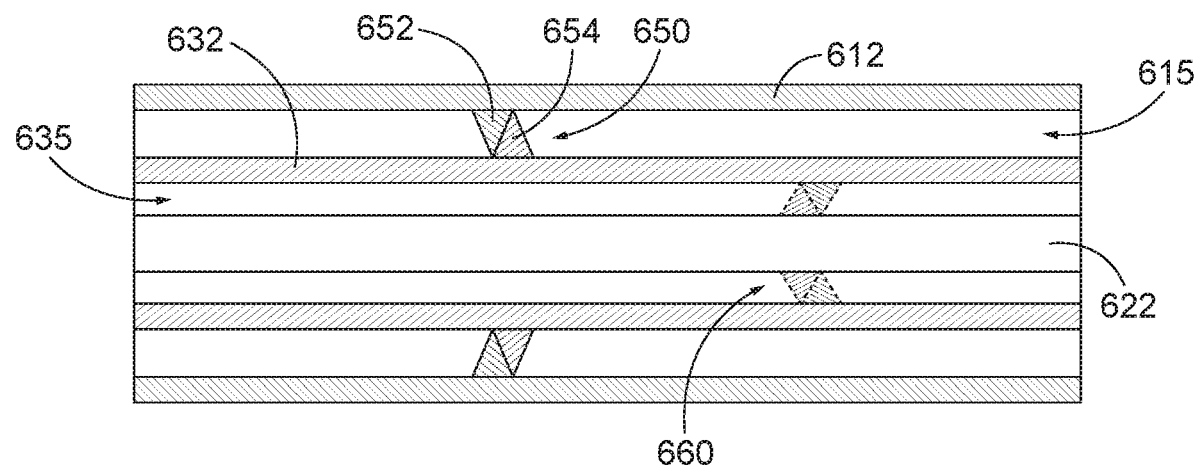
FIG. 23A depicts a cross-sectional view of the distal portion of the reusable sub-assembly of FIG. 18 taken along a centerline thereof, showing the reusable sub-assembly coupled with the outer tube.

In use, during a surgical procedure, outer tube (612) is positioned about inner tube (632) and ultrasonic blade (622), as shown in FIG. 23A. In this assembled configuration, inner seal (652) of outer tube (612) engages outer seal (654) of inner tube (632) to form split seal (650) between a distal portion of outer tube (612) and inner tube (632). For instance, proximal wall (653) of inner seal (652) abuts distal wall (659) of outer seal (654). Tip (651) of inner seal (652) extends into opening (615) to engage an outer surface of inner tube (632) and/or tip (657) of outer seal (654) extends into opening (615) to engage an inner surface of outer tube (612). In some versions, inner seal (652) and/or outer seal (654) elastically deforms when outer tube (612) is assembled with inner tube (632). Split seal (650) thereby extends between inner tube (632) and outer tube (612) to seal a distal portion of opening (615) of outer tube (612). This inhibits bodily fluid from entering distally between inner tube (632) and outer tube (612). In some versions, an alternative split seal (660), similar to split seal (650) described above, may be positioned between inner tube (632) and ultrasonic blade (622). Such alternative split seal (660) may be used with or with split seal (650).

Figure 23B:
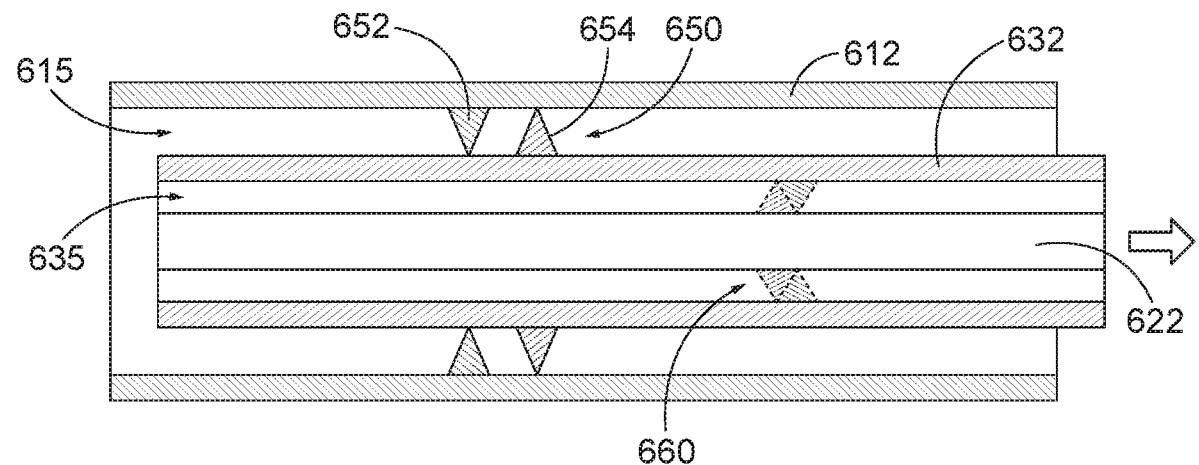
FIG. 23B depicts the cross-sectional view of the distal portion of the reusable sub-assembly similar to FIG. 23A, but showing the reusable sub-assembly being removed from the outer tube.

After the surgical procedure, outer tube (612) is removed from inner tube (632) and ultrasonic blade (622), as shown in FIG. 23B, to thereby separate inner seal (652) and outer seal (654). With split seal (650) separated, inner tube (632) and ultrasonic blade (622) are sterilized. During sterilization, sterilization fluid, such as sterilization gas, diffuses between inner tube (632) and ultrasonic blade (622) through opening (635) of inner tube (632) to effectively sterilize ultrasonic blade (622). Once sterilization is complete, inner tube (632) and ultrasonic blade (622) are coupled with another outer tube (612) and inner seal (652) for reuse. Still other suitable configurations for split seal (650) will be apparent to one of ordinary skill in the art in view of the teachings herein.

E. Exemplary Inner Tube Removable Seal

Figure 24:
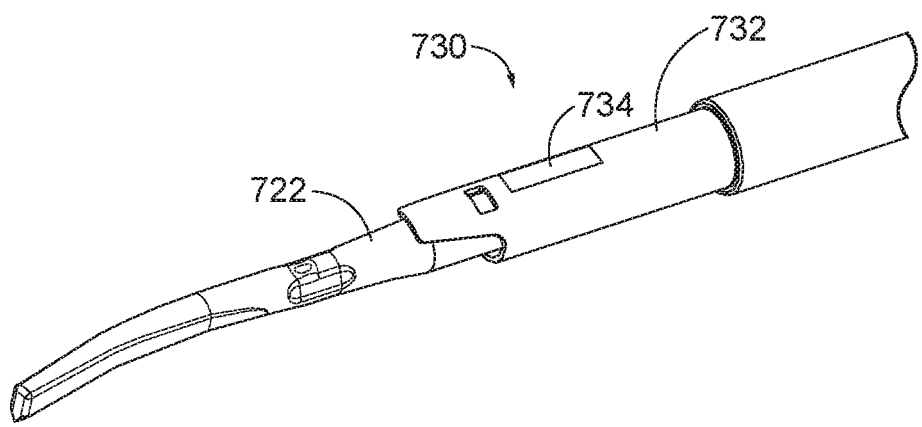
FIG. 24 depicts a perspective view of a distal end portion of a fifth exemplary reusable sub-assembly.
Figure 25:
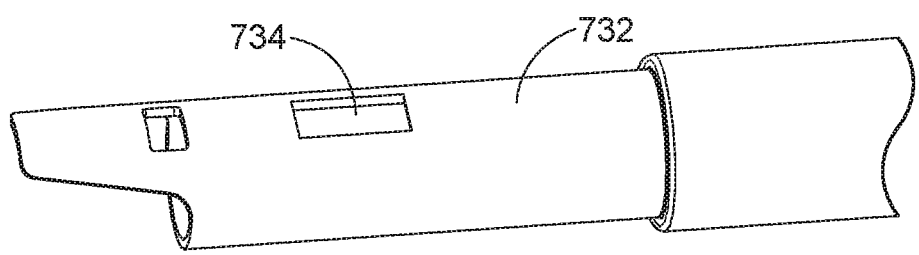
FIG. 25 depicts a perspective view of a distal end portion of an inner tube of the reusable sub-assembly of FIG. 24.
Figure 26:
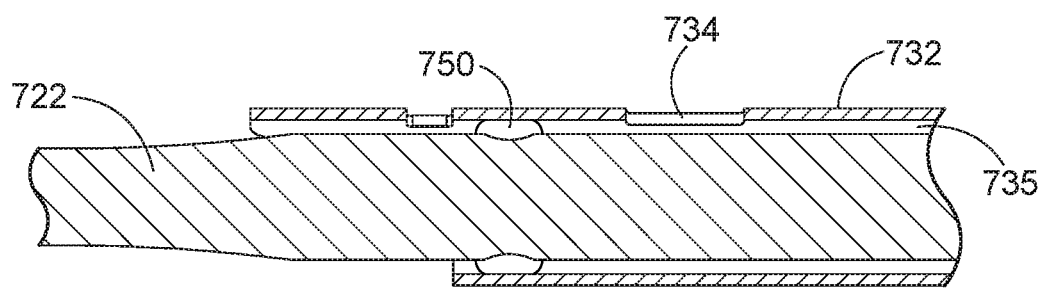
FIG. 26 depicts a cross-sectional view of the distal portion of the reusable sub-assembly of FIG. 24 taken along a centerline thereof.

Referring to FIGS. 24-26, a fifth exemplary reusable sub-assembly (730) is shown that is similar to reusable sub-assembly (230) (see FIG. 3) described above, except that reusable sub-assembly (730) comprises distal opening (734) extending through a distal top portion of inner tube (732). In the illustrated example, distal opening (734) is generally rectangular, but other suitable shapes may be used (e.g., square, circular, oval, etc.). In some versions, reusable sub-assembly (730) may include inner seal (750), similar to inner seal (450) (see FIG. 3) described above, between a distal portion of inner tube (732) and ultrasonic blade (722). Distal opening (734) is positioned proximal to inner seal (750), as shown in FIG. 25. Distal opening (734) allows fluid to enter through distal opening (734) of inner tube (732) to ultrasonic blade (722) positioned within inner tube (732) during sterilization. Distal opening (734) then selectively seals with removable seal (760), such as during a surgical procedure.

Figure 27:
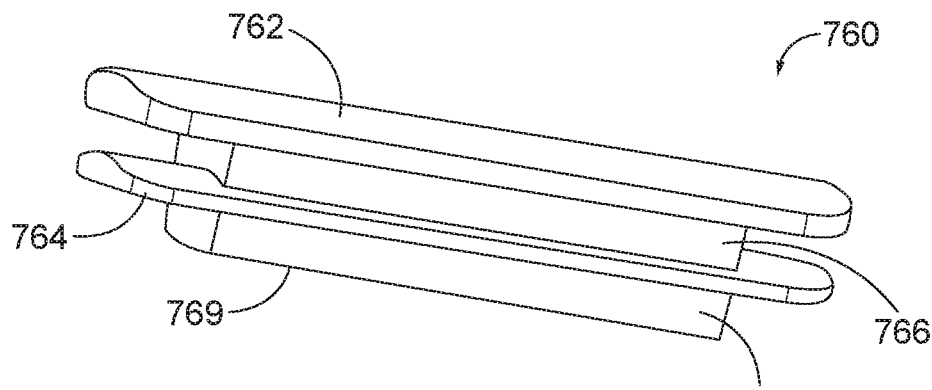
FIG. 27 depicts a perspective view of a seal for use with the reusable sub-assembly of FIG. 24.
Figure 28:
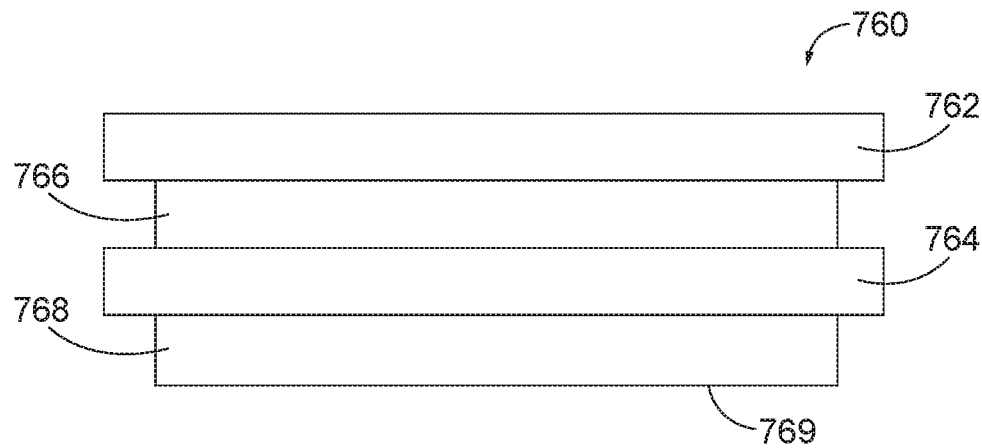
FIG. 28 depicts a side elevational view of the seal of FIG. 27.
Figure 29:
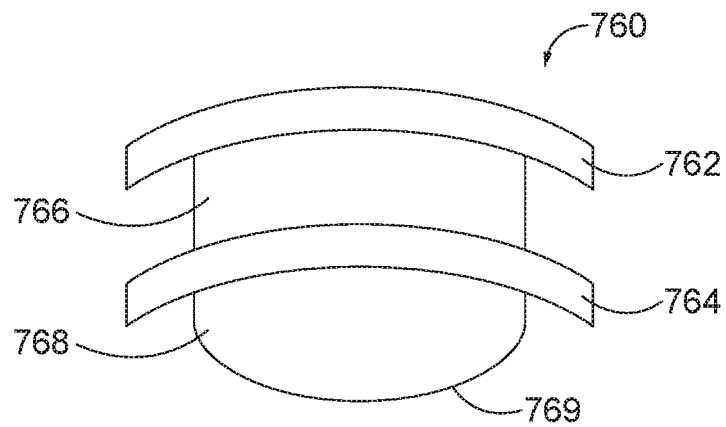
FIG. 29 depicts an end view of the seal of FIG. 27.

Removable seal (760), as shown in FIGS. 27-29, comprises upper flange (762) and lower flange (764) positioned beneath upper flange (762). Upper sealing member (766) is positioned between upper flange (762) and lower flange (764). Lower sealing member (768) then extends beneath lower flange (764) to define bottom surface (769). Upper and lower sealing members (766, 768) each have a smaller length and/or width than upper and lower flanges (762, 764). Removable seal (760) is sized to correspond to distal opening (734) (see FIG. 25) and defines a generally arcuate shape to correspond with the circular profile of inner tube (732) (see FIG. 25). Removable seal (760) may be configured to be reusable with reusable sub-assembly (730) or to be disposable such that a new removable seal (760) is used with each surgical procedure.

Figure 30:
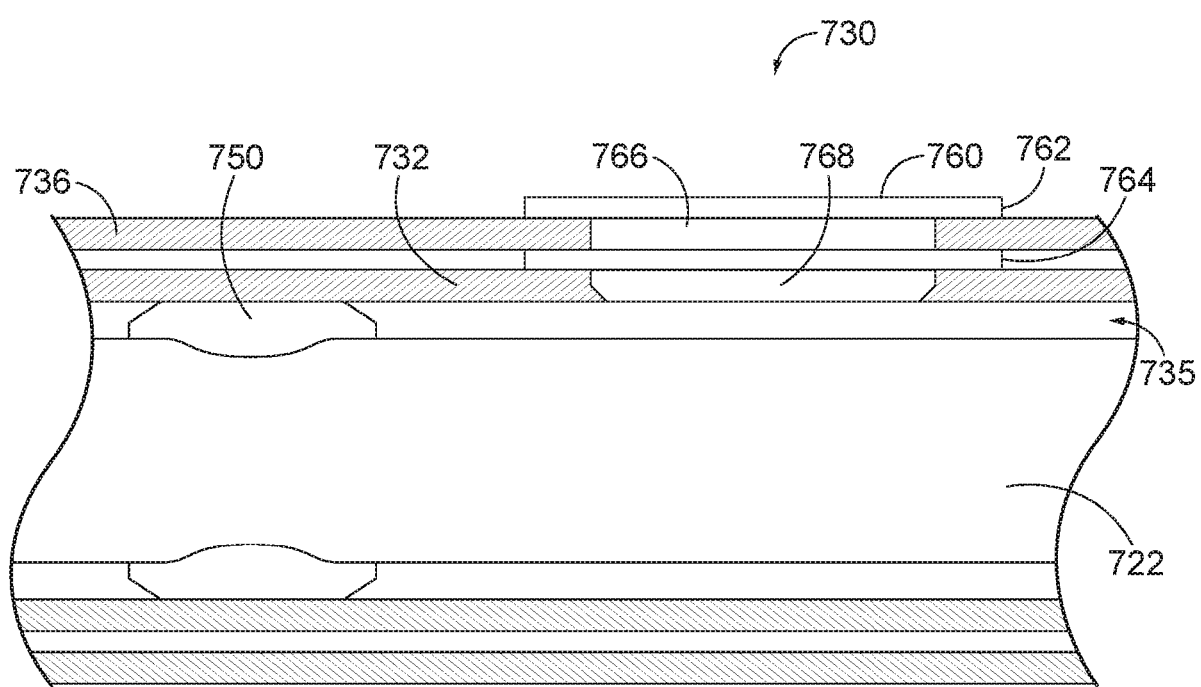
FIG. 30 depicts a cross-sectional view of the distal portion of the reusable sub-assembly of FIG. 24 coupled with the seal of FIG. 27.

In use, during a surgical procedure, removable seal (760) is positioned within opening (734) of inner tube (732), as shown in FIG. 30. In this assembled configuration, opening (734) of inner tube (732) is aligned with opening (770) of distal inner tube (736). Removable seal (760) is then inserted within both openings such that upper flange (762) is positioned on an outer surface of distal inner tube (736), upper sealing member (766) is positioned within opening (770) of distal inner tube (736), lower flange (764) is positioned between distal inner tube (736) and inner tube (732), and lower sealing member (768) is positioned within opening (734) of inner tube (732). In some other versions, upper flange (762) and upper sealing member (766) may be removed such that removable seal (760) is only coupled with inner tube (732). Accordingly, longitudinal opening (735) through inner tube (732) is sealed at a distal portion by inner seal (750) and by removable seal (760). This inhibits bodily fluid from entering distally through inner tube (732). Removable seal (760) may also inhibit a loss of insufflation in the event that such pressurized anatomies are present during the surgical procedure.

After the surgical procedure, removable seal (760) is removed from inner tube (732) to thereby uncover opening (734) of inner tube (732). This allows inner tube (732) and ultrasonic blade (722) to be sterilized. During sterilization, sterilization fluid, such as a sterilization gas, diffuses between inner tube (732) and ultrasonic blade (722) through opening (734) of inner tube (732) to effectively sterilize ultrasonic blade (722). Once sterilization is complete, removable seal (760) is reassembled with inner tube (732) for reuse. Still other suitable configurations for removable seal (750) will be apparent to one of ordinary skill in the art in view of the teachings herein.

Figure 31:
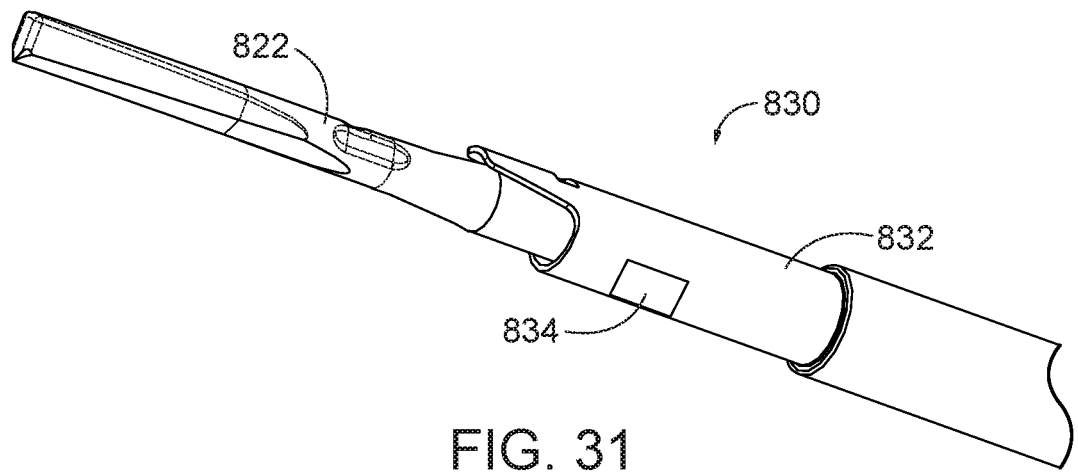
FIG. 31 depicts a perspective view of a distal end portion of a sixth exemplary reusable sub-assembly.
Figure 32:
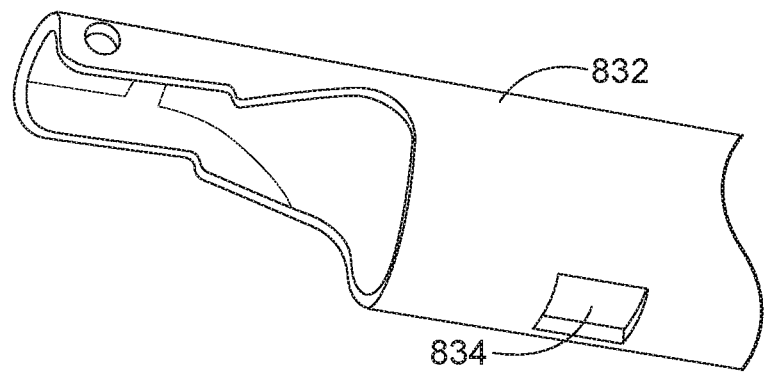
FIG. 32 depicts a perspective view of a distal end portion of an inner tube of the reusable sub-assembly of FIG. 31.
Figure 33:
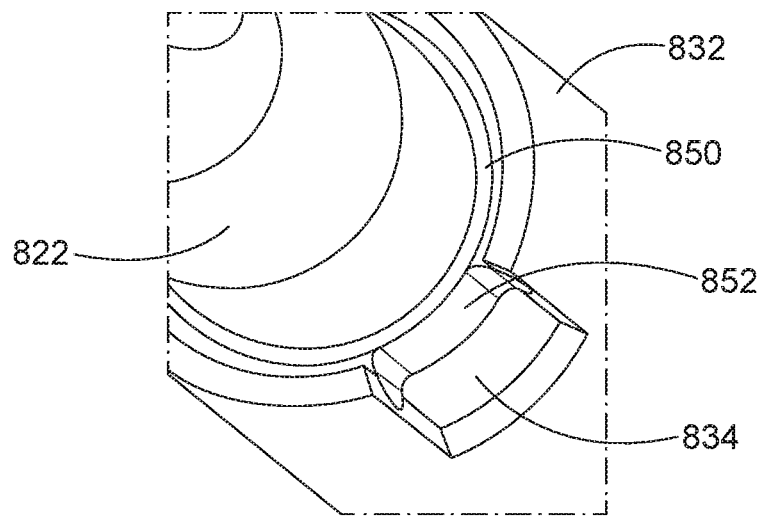
FIG. 33 depicts an enlarged, sectional, perspective view of the distal portion of the reusable sub-assembly of FIG. 31.

By way of further example, referring to FIGS. 31-33, a sixth exemplary reusable sub-assembly (830) is shown that is similar to reusable sub-assembly (730) (see FIG. 24) described above, except that reusable sub-assembly (830) comprises distal opening (834) extending through a distal bottom portion of inner tube (832) aligned with inner seal (850). In the illustrated example, distal opening (834) is generally rectangular, but other suitable shapes may be used (e.g., square, circular, oval, etc.). Because distal opening (834) is aligned with inner seal (850), inner seal (850) of the present example includes a cutout (852) at a bottom portion of inner seal (850) to receive a portion of removable seal (860). Distal opening (834) and/or cutout (852) thereby allows gas or fluid to enter through distal opening (834) and/or cutout (852) to ultrasonic blade (822) positioned within inner tube (832) during sterilization. Distal opening (834) and/or cutout (852) is then selectively sealed with removable seal (860), such as during a surgical procedure.

Figure 34:
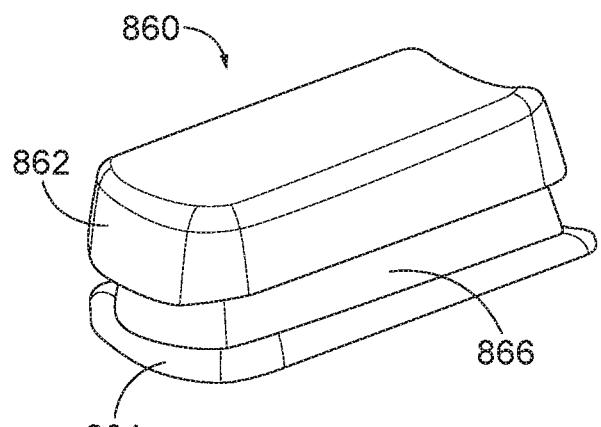
FIG. 34 depicts a perspective view of a seal for use with the reusable sub-assembly of FIG. 31.
Figure 35:
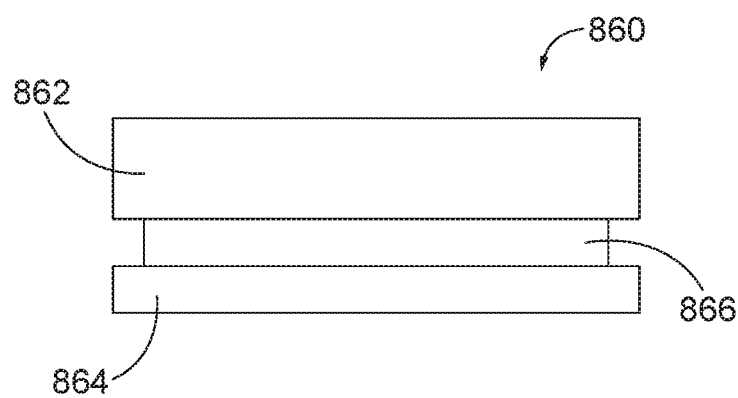
FIG. 35 depicts a side elevational view of the seal of FIG. 34.
Figure 36:
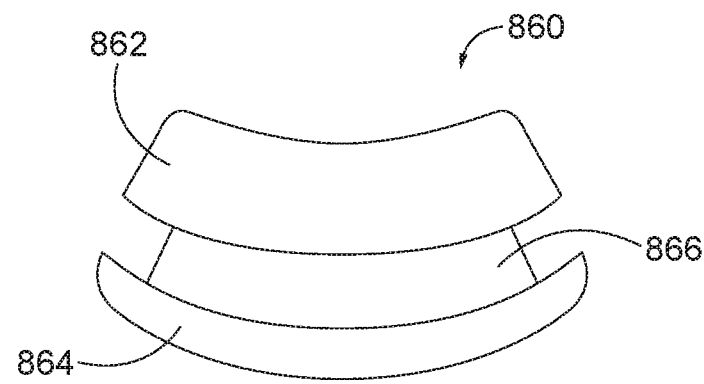
FIG. 36 depicts an end view of the seal of FIG. 34.

Removable seal (860), as shown in FIGS. 34-36, comprises upper flange (862) and lower flange (864) positioned beneath upper flange (862). Sealing member (866) is positioned between upper flange (862) and lower flange (864). Sealing member (866) has a smaller length and/or width than upper and lower flanges (862, 864). Removable seal (860) is sized to correspond to distal opening (834) and defines a generally arcuate shape to correspond with the circular profile of inner tube (832) (see FIG. 32). Removable seal (860) may be configured to be reusable with reusable sub-assembly (830) or to be disposable such that a new reusable seal (860) is used with each surgical procedure.

Figure 37:
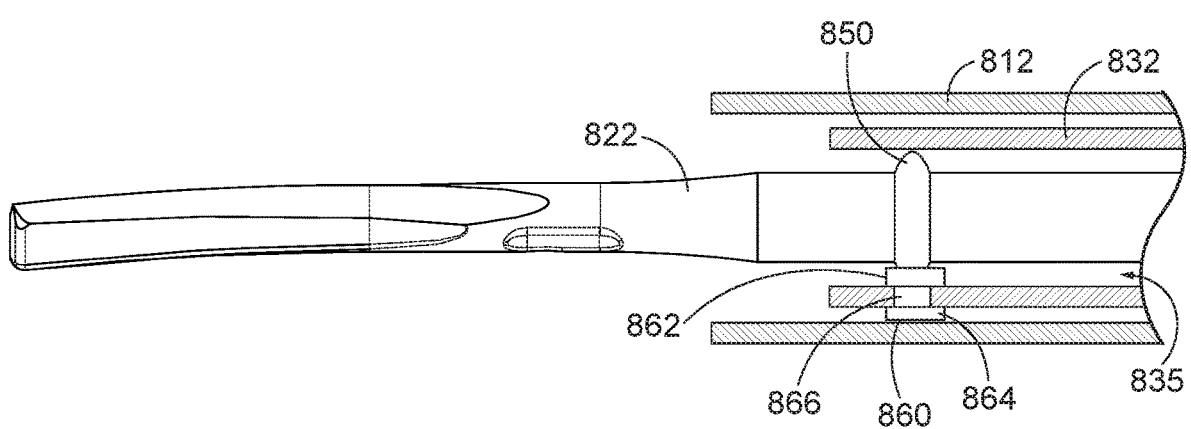
FIG. 37 depicts a sectional view of the distal end portion of the reusable sub-assembly of FIG. 31, taken generally along a centerline thereof, coupled with an outer tube.

In use, during a surgical procedure, removable seal (860) is positioned within opening (834) of inner tube (832), as shown in FIG. 37. In this assembled configuration, removable seal (860) is inserted within inner tube (832) such that upper flange (862) is positioned within longitudinal opening (835) of inner tube (832) and against inner seal (850) within cutout (852). Sealing member (866) is then positioned within the opening (834) of inner tube (832) and lower flange (864) is positioned between inner tube (832) and outer tube (812). Accordingly, longitudinal opening (835) through inner tube (832) is sealed at a distal portion by inner seal (850) and by removable seal (860). This inhibits bodily fluid from entering distally through inner tube (832).

After the surgical procedure, removable seal (860) is removed from inner tube (832) to thereby uncover opening (834) of inner tube (832). This allows inner tube (832) and ultrasonic blade (822) to be sterilized. During sterilization, sterilization fluid, such as sterilization gas, diffuses between inner tube (832) and ultrasonic blade (822) through opening (834) of inner tube (832) to effectively sterilize ultrasonic blade (822). Once sterilization is complete, removable seal (860) is reassembled with inner tube (832) for reuse.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a first assembly, including: (i) an inner tube having at least one opening, an exterior, and an interior and (ii) an ultrasonic blade positioned within the inner tube; and (b) a second assembly, including: (i) an outer tube, and (ii) a seal, wherein the first assembly is selectively couplable with the second assembly to form an assembled configuration such that the inner tube in the assembled configuration is positioned within the outer tube and the seal is coupled with the at least one opening of the inner tube thereby selectively fluidly sealing the at least one opening of the inner tube, and wherein the first assembly is selectively decouplable from the second assembly to form a dis-assembled configuration such that the at least one opening of the inner tube in the dis-assembled configuration is fluidly open and thereby configured to receive a sterilization fluid therethrough from the exterior of the inner tube to the interior of inner tube for sterilizing the ultrasonic blade within the inner tube.

Example 2

The surgical instrument of Example 1, wherein the inner tube has a sidewall extending between the exterior and the interior, and wherein the at least one opening of the inner tube includes a plurality of perforations extending through the sidewall of the inner tube.

Example 3

The surgical instrument of Example 2, wherein the plurality of perforations has a longitudinally aligned row of perforations longitudinally spaced along the inner tube.

Example 4

The surgical instrument of any one or more of Examples 2 through 3, wherein the seal includes an outer seal arranged about the inner tube and distally positioned from the plurality of perforations, and wherein the outer seal has at least one sealing member extending between an outer surface of the inner tube and an inner surface of the outer tube.

Example 5

The surgical instrument any one or more of Examples 1 through 4, wherein the at least one opening includes an open distal end of the inner tube, wherein the seal includes a body defining a distal seal opening and a proximal seal opening, wherein the proximal seal opening has a larger outer diameter than the distal opening, and wherein the seal is positioned about the open distal end of the inner tube such that the open distal end of the inner tube is inserted within the proximal seal opening and the ultrasonic blade is inserted through the distal seal opening.

Example 6

The surgical instrument of Example 5, wherein the seal in the assembled configuration couples with an inner surface of the outer tube.

Example 7

The surgical instrument any one or more of Examples 1 through 6, wherein the seal includes a split seal having a first seal portion and a second seal portion, wherein the first portion is positioned about an inner circumference of the outer tube, wherein the second portion is positioned about an outer circumference of the inner tube, and wherein the first seal portion is configured to removably engage against the second seal portion fluidly sealing the split seal therethrough.

Example 8

The surgical instrument of Example 7, wherein the first seal portion and the second seal portion of the split seal each have a generally triangular shape such that the first seal portion defines a first wall transverse to a longitudinal axis of the outer tube and the second seal portion defines a second wall transverse to the longitudinal axis, and wherein the first and second walls are configured to removably engage thereby fluidly sealing the split seal.

Example 9

The surgical instrument any one or more of Examples 1 through 8, wherein the inner tube has a sidewall extending between the exterior and the interior and the at least one opening of the inner tube extends through the sidewall, wherein the seal includes a flange and a sealing member adjacent to the flange, and wherein the flange is positionable about an exterior surface of the sidewall such that the sealing member is within the at least one opening of the sidewall to selectively fluidly seal the at least one opening in the assembled configuration.

Example 10

The surgical instrument of Example 9, wherein the first assembly further includes an inner seal positioned between the inner tube and the ultrasonic blade, wherein the inner seal has a cutout, and wherein at least a portion of the sealing member is positioned within the cutout of the inner seal.

Example 11

The surgical instrument any one or more of Examples 1 through 10, wherein the first assembly further includes a sterilization detection system, having: (i) a thermal switch configured to move from an open state to a closed state when the thermal switch is above a predetermined temperature threshold, (ii) a clock operatively connected to the thermal switch and configured to measure an elapsed time when the thermal switch is in the closed state, and (iii) a controller operatively connected to the clock and configured to determine whether a sterilization cycle has occurred based on the elapsed time measured by the clock.

Example 12

The surgical instrument of Example 11, wherein the sterilization detection system further includes a memory operatively connected to the controller and configured to store a sterilization condition, and wherein the controller is further configured to determine whether the sterilization cycle has occurred based on the sterilization condition.

Example 13

The surgical instrument any one or more of Examples 11 through 12, wherein the controller is further configured to determine a cumulative number of sterilization cycles that have been performed on the first assembly.

Example 14

The surgical instrument any one or more of Examples 11 through 13, wherein the controller is further configured to determine a sterilization cycle type that has been performed on the first assembly from a plurality of predetermined sterilization cycle types.

Example 15

The surgical instrument any one or more of Examples 1 through 14, wherein the first assembly is a reusable assembly, and wherein the second assembly is a disposable assembly.

Example 16

A reusable assembly of a surgical instrument, comprising: (a) an inner tube including at least one opening; (b) an ultrasonic blade positioned within the inner tube, wherein the at least one opening of the inner tube is fluidly open and thereby configured to receive a sterilization fluid therethrough from an exterior of the inner tube to the interior of the inner tube for sterilizing the ultrasonic blade within the inner tube; and (c) a sterilization detection system, including: (i) a thermal switch configured to move from an open state to a closed state when the thermal switch is above a predetermined temperature threshold, (ii) a clock operatively connected to the thermal switch and configured to measure an elapsed time when the thermal switch is in the closed state, and (iii) a controller operatively connected to the clock and configured to determine whether a sterilization cycle has occurred based on elapsed time measured by the clock.

Example 17

The reusable assembly of Example 16, further comprising a seal selectively couplable with the at least one opening of the inner tube, and wherein the seal is configured to fluidly seal the at least one opening of the inner tube for inhibiting bodily fluid from entering the at least one opening during a surgical procedure.

Example 18

A method of determining that a reusable portion of a surgical instrument has been sterilized, comprising: (a) closing a thermal switch to a closed state when the reusable portion is subjected to a higher temperature above a predetermined temperature threshold; (b) measuring an elapsed time when the reusable portion is above the predetermined temperature threshold; (c) opening the thermal switch to an opened state when the reusable portion decreases from the higher temperature to a lower temperature less than or equal to the predetermined temperature threshold to thereby stop measuring the elapsed time; and (d) comparing the measured elapsed time to a sterilization condition to thereby determine that the reusable portion has been sterilized during a sterilization cycle.

Example 19

The method of Example 18, further comprising determining a cumulative number of the sterilization cycles that have been performed on the reusable portion.

Example 20

The method of any one or more of Examples 18 through 19, further comprising determining a sterilization cycle type that has been performed on the reusable portion from a plurality of predetermined sterilization cycle types.

V. MISCELLANEOUS

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; 8,911,460; 9,095,367; 9,381,058; 9,393,037; 10,172,636; U.S. Pub. No. 2006/0079874, now abandoned; U.S. Pub. No. 2007/0191713, now abandoned;

U.S. Pub. No. 2007/0282333, now abandoned; U.S. Pub. No. 2008/0200940, now abandoned; U.S. Pub. No. 2012/0116265, now abandoned; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
 (a) a first assembly, including:
  (i) an inner tube extending from an inner distal end portion to an inner proximal end portion and having at least one opening, an exterior, and an interior, wherein the at least one opening is positioned in the inner distal end portion of the inner tube, and
  (ii) an ultrasonic blade having an acoustic waveguide proximally extending therefrom, wherein the acoustic waveguide extends through the inner tube such that the ultrasonic blade distally projects relative to the inner distal end portion of the inner tube; and (b) a second assembly, including:
(i) an outer tube extending from an outer distal end portion to an outer proximal end portion, and
(ii) a seal positioned at the outer distal end portion of the outer tube, wherein the first assembly is selectively couplable with the second assembly to form an assembled configuration, wherein the inner distal end portion is received within the outer distal end portion in the assembled configuration such that the inner tube is positioned within the outer tube and the seal is fluidly coupled with the at least one opening of the inner tube thereby selectively fluidly sealing the at least one opening of the inner tube, and wherein the first assembly is selectively decouplable from the second assembly to form a dis-assembled configuration such that the at least one opening of the inner tube in the dis-assembled configuration is fluidly open and thereby configured to receive a sterilization fluid therethrough from the exterior of the inner tube to the interior of inner tube for sterilizing the ultrasonic blade within the inner tube.

2. The surgical instrument of claim 1, wherein the inner tube has a sidewall extending between the exterior and the interior, and wherein the at least one opening of the inner tube includes a plurality of perforations extending through the sidewall of the inner tube.

3. The surgical instrument of claim 2, wherein the plurality of perforations has a longitudinally aligned row of perforations longitudinally spaced along the inner tube.

4. The surgical instrument of claim 2, wherein the seal includes an outer seal arranged about the inner tube and distally positioned from the plurality of perforations, and wherein the outer seal has at least one sealing member extending between an outer surface of the inner tube and an inner surface of the outer tube.

5. The surgical instrument of claim 1, wherein the at least one opening includes an open distal end of the inner tube, wherein the seal includes a body defining a distal seal opening and a proximal seal opening, wherein the proximal seal opening has a larger outer diameter than the distal opening, and wherein the seal is positioned about the open distal end of the inner tube such that the open distal end of the inner tube is inserted within the proximal seal opening and the ultrasonic blade is inserted through the distal seal opening.

6. The surgical instrument of claim 5, wherein the seal in the assembled configuration couples with an inner surface of the outer tube.

7. The surgical instrument of claim 1, wherein the seal includes a split seal having a first seal portion and a second seal portion, wherein the first portion is positioned about an inner circumference of the outer tube, wherein the second portion is positioned about an outer circumference of the inner tube, and wherein the first seal portion is configured to removably engage against the second seal portion fluidly sealing the split seal therethrough.

8. The surgical instrument of claim 7, wherein the first seal portion and the second seal portion of the split seal each have a generally triangular shape such that the first seal portion defines a first wall transverse to a longitudinal axis of the outer tube and the second seal portion defines a second wall transverse to the longitudinal axis, and wherein the first and second walls are configured to removably engage thereby fluidly sealing the split seal.

9. The surgical instrument of claim 1, wherein the inner tube has a sidewall extending between the exterior and the interior and the at least one opening of the inner tube extends through the sidewall, wherein the seal includes a flange and a sealing member adjacent to the flange, and wherein the flange is positionable about an exterior surface of the sidewall such that the sealing member is within the at least one opening of the sidewall to selectively fluidly seal the at least one opening in the assembled configuration.

10. The surgical instrument of claim 1, wherein the first assembly further includes a sterilization detection system, having:
(i) a thermal switch configured to move from an open state to a closed state when the thermal switch is above a predetermined temperature threshold,
(ii) a clock operatively connected to the thermal switch and configured to measure an elapsed time when the thermal switch is in the closed state, and
(iii) a controller operatively connected to the clock and configured to determine whether a sterilization cycle has occurred based on the elapsed time measured by the clock.

11. The surgical instrument of claim 10, wherein the sterilization detection system further includes a memory operatively connected to the controller and configured to store a sterilization condition, and wherein the controller is further configured to determine whether the sterilization cycle has occurred based on the sterilization condition.

12. The surgical instrument of claim 10, wherein the controller is further configured to determine a cumulative number of sterilization cycles that have been performed on the first assembly.

13. The surgical instrument of claim 10, wherein the controller is further configured to determine a sterilization cycle type that has been performed on the first assembly from a plurality of predetermined sterilization cycle types.

14. The surgical instrument of claim 1, wherein the first assembly is a reusable assembly, and wherein the second assembly is a disposable assembly.

15. The surgical instrument of claim 1, wherein the outer distal end portion of the outer tube radially covers the at least one opening in the inner distal end portion of the inner tube thereby further selectively fluidly sealing the at least one opening of the inner tube.

16. A reusable assembly of a surgical instrument, comprising:
(a) an inner tube including at least one opening;
(b) an ultrasonic blade positioned within the inner tube, wherein the at least one opening of the inner tube is fluidly open and thereby configured to receive a sterilization fluid therethrough from an exterior of the inner tube to the interior of the inner tube for sterilizing the ultrasonic blade within the inner tube; and
(c) a sterilization detection system, including:
(i) a thermal switch configured to move from an open state to a closed state when the thermal switch is above a predetermined temperature threshold,
(ii) a clock operatively connected to the thermal switch and configured to measure an elapsed time when the thermal switch is in the closed state, and
(iii) a controller operatively connected to the clock and configured to determine whether a sterilization cycle has occurred based on the elapsed time measured by the clock.

17. The reusable assembly of the surgical instrument of claim 16, further comprising a seal selectively couplable with the at least one opening of the inner tube, and wherein the seal is configured to fluidly seal the at least one opening of the inner tube for inhibiting bodily fluid from entering the at least one opening during a surgical procedure.

\* \* \* \* \*